United States Patent
Yang

(10) Patent No.: US 10,219,764 B2
(45) Date of Patent: Mar. 5, 2019

(54) RECEIVING DEVICE AND X-RAY IMAGING APPARATUS HAVING THE SAME

(71) Applicant: SAMSUNG ELECTRONICS CO., LTD., Suwon-si (KR)

(72) Inventor: Chang Jin Yang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 41 days.

(21) Appl. No.: 14/861,436

(22) Filed: Sep. 22, 2015

(65) Prior Publication Data

US 2016/0120489 A1 May 5, 2016

(30) Foreign Application Priority Data

Sep. 23, 2014 (KR) .................. 10-2014-0127201

(51) Int. Cl.
*A61B 6/00* (2006.01)
*A61B 6/10* (2006.01)

(52) U.S. Cl.
CPC .......... *A61B 6/4405* (2013.01); *A61B 6/4266* (2013.01); *A61B 6/4283* (2013.01); *A61B 6/102* (2013.01)

(58) Field of Classification Search
CPC .... A61B 6/4266; A61B 6/4283; A61B 6/4405
USPC .................. 378/98.8, 189, 197, 198
See application file for complete search history.

(56) References Cited

U.S. PATENT DOCUMENTS

| | | | |
|---|---|---|---|
| 5,138,160 A | 8/1992 | Shimizu et al. | |
| 5,473,664 A * | 12/1995 | Strawder | G03B 42/025 378/167 |
| 6,296,386 B1 * | 10/2001 | Heidsieck | G03B 42/04 378/182 |
| 6,533,453 B1 * | 3/2003 | Heidsieck | G01T 1/2928 378/189 |
| 6,592,257 B1 * | 7/2003 | Heidsieck | A61B 6/502 378/189 |
| 7,016,467 B2 * | 3/2006 | Brooks | A61B 6/563 378/102 |

(Continued)

FOREIGN PATENT DOCUMENTS

| | | |
|---|---|---|
| JP | 2006-85082 | 3/2006 |
| JP | 2006-296676 | 11/2006 |

OTHER PUBLICATIONS

International Search Report dated Jan. 28, 2016 in corresponding International Patent Application No. PCT/KR2015/009882.

(Continued)

*Primary Examiner* — Allen C. Ho
(74) *Attorney, Agent, or Firm* — Staas & Halsey LLP

(57) ABSTRACT

A receiving device in which detectors of different sizes can be stably accommodated and an X-ray imaging apparatus having the same are provided. A receiving device having a receiving unit in which a first detecting device is accommodated. The receiving device includes a fixing unit provided in the receiving unit and into which a part of a side surface of the first detecting device is inserted in order to prevent the first detecting device from being moved; and a detector support having a side that is connected to a rotating shaft and tiltable, and configured to support at least one side surface of a second detecting device having a smaller size than the first detecting device.

22 Claims, 18 Drawing Sheets

(56) References Cited

U.S. PATENT DOCUMENTS

| | | | | |
|---|---|---|---|---|
| 7,097,355 B2* | 8/2006 | Araki | A61B 6/4283 | 378/167 |
| 7,108,421 B2* | 9/2006 | Gregerson | A61B 6/032 | 378/146 |
| 7,137,735 B2* | 11/2006 | Araki | A61B 6/4283 | 378/167 |
| 7,144,158 B2* | 12/2006 | Dippl | G03B 42/02 | 378/167 |
| 7,365,337 B2* | 4/2008 | Tsuchino | A61B 6/56 | 250/370.09 |
| 7,438,470 B2* | 10/2008 | Koren | A61B 6/00 | 378/198 |
| 7,545,914 B2* | 6/2009 | Kito | A61B 6/4283 | 378/207 |
| 7,573,034 B2* | 8/2009 | Heath | A61B 6/4494 | 250/361 R |
| 7,575,373 B2* | 8/2009 | Xu | A61B 6/00 | 378/169 |
| 7,581,883 B2* | 9/2009 | Kato | G03B 42/02 | 378/167 |
| 7,611,282 B2* | 11/2009 | Koren | A61B 6/4233 | 378/198 |
| 7,764,765 B2* | 7/2010 | Ohta | A61B 6/4233 | 250/370.09 |
| 7,775,712 B1* | 8/2010 | Thieman | G03B 42/04 | 378/186 |
| 7,785,005 B2* | 8/2010 | Bettouyashiki | G03B 42/025 | 320/107 |
| 7,828,481 B2* | 11/2010 | Ye | A61B 6/0457 | 378/117 |
| 7,857,511 B2* | 12/2010 | Hesl | A61B 6/4233 | 378/189 |
| 7,866,163 B2* | 1/2011 | Ertel | G01T 1/2928 | 62/3.2 |
| 7,881,435 B2* | 2/2011 | Wu | A61B 6/4283 | 250/370.09 |
| 7,909,511 B2* | 3/2011 | Hall | A61B 6/4233 | 378/189 |
| 7,956,330 B2* | 6/2011 | Nishino | A61B 6/00 | 250/370.09 |
| 7,988,356 B2* | 8/2011 | Watanabe | A61B 6/00 | 378/189 |
| 8,021,045 B2* | 9/2011 | Foos | A61B 6/4405 | 378/198 |
| 8,107,590 B2* | 1/2012 | Nishino | A61B 6/4494 | 250/370.09 |
| 8,182,147 B2* | 5/2012 | Nishino | A61B 6/00 | 378/189 |
| 8,186,879 B2* | 5/2012 | Li | A61B 6/4283 | 378/189 |
| 8,194,823 B2* | 6/2012 | Ohta | A61B 6/4233 | 250/370.09 |
| 8,256,957 B1* | 9/2012 | Barnes | G01T 7/00 | 378/154 |
| 8,292,504 B2* | 10/2012 | Bettouyashiki | G03B 42/025 | 320/107 |
| 8,319,506 B2* | 11/2012 | Liu | A61B 6/4283 | 324/691 |
| 8,325,875 B2* | 12/2012 | Omernick | A61B 6/42 | 378/62 |
| 8,364,241 B2* | 1/2013 | Hannon | A61B 6/4494 | 378/114 |
| 8,396,188 B2* | 3/2013 | Liu | A61B 6/4233 | 378/62 |
| 8,401,150 B2* | 3/2013 | Watanabe | A61B 6/4283 | 378/114 |
| 8,425,176 B2* | 4/2013 | Forcina | G03B 42/045 | 221/113 |
| 8,485,726 B2* | 7/2013 | Kobayashi | A61B 6/4233 | 250/370.09 |
| 8,571,173 B2* | 10/2013 | Hoffmann | A61B 6/502 | 378/189 |
| 8,576,986 B2* | 11/2013 | Liu | G01T 1/247 | 250/584 |
| 8,591,106 B2* | 11/2013 | Nishino | A61B 6/4233 | 378/189 |
| 8,616,766 B2* | 12/2013 | Takahashi | G03B 42/04 | 378/189 |
| 8,618,491 B2* | 12/2013 | Shimizukawa | A61B 6/4233 | 250/370.09 |
| 8,622,614 B2* | 1/2014 | Carmichael | A61B 6/4266 | 378/198 |
| 8,678,649 B2* | 3/2014 | Bechard | A61B 6/00 | 378/198 |
| 8,714,817 B2* | 5/2014 | Oyaizu | G03B 42/04 | 378/189 |
| 8,721,176 B2* | 5/2014 | McBroom | A61B 6/4283 | 378/189 |
| 8,723,131 B2* | 5/2014 | Kobayashi | G03B 42/02 | 250/370.01 |
| 8,727,619 B2* | 5/2014 | Yamamichi | A61B 6/4494 | 378/207 |
| 8,729,484 B2* | 5/2014 | Nishino | G01T 1/2018 | 250/370.09 |
| 8,735,829 B2* | 5/2014 | Kuwabara | A61B 6/4233 | 250/362 |
| 8,742,354 B2* | 6/2014 | Shimizukawa | A61B 6/4233 | 250/354.1 |
| 8,768,035 B2* | 7/2014 | Liu | A61B 6/585 | 378/62 |
| 8,829,455 B2* | 9/2014 | Nakatsugawa | A61B 6/4283 | 250/370.09 |
| 8,834,022 B2* | 9/2014 | Koyanagi | A61B 6/56 | 250/370.09 |
| 8,841,628 B2* | 9/2014 | Kitano | H01L 27/14663 | 250/393 |
| 8,848,872 B2* | 9/2014 | Lee | G03B 42/04 | 250/370.09 |
| 8,851,750 B2* | 10/2014 | Lee | G03B 42/04 | 378/189 |
| 8,855,691 B2* | 10/2014 | Kamiya | A61B 6/4283 | 340/2.1 |
| 8,861,678 B2* | 10/2014 | Liu | H05G 1/08 | 378/91 |
| 8,866,096 B2* | 10/2014 | Eguchi | A61B 6/00 | 250/370.08 |
| 8,891,733 B2* | 11/2014 | Liu | A61B 6/42 | 378/91 |
| 8,942,444 B2* | 1/2015 | Liu | A61B 6/563 | 128/922 |
| 8,956,045 B2* | 2/2015 | Tajima | A61B 6/4283 | 378/145 |
| 8,961,011 B2* | 2/2015 | Lalena | A61B 6/4405 | 378/197 |
| 8,975,868 B2* | 3/2015 | Konkle | A61B 6/4283 | 320/115 |
| 9,001,972 B2* | 4/2015 | Takahashi | H05G 1/30 | 378/62 |
| 9,041,351 B2* | 5/2015 | Ikegame | H02J 7/0045 | 320/107 |
| 9,044,191 B2* | 6/2015 | Nishino | A61B 6/4405 | |
| 9,050,051 B2* | 6/2015 | Nakatsugawa | G01T 1/24 | |
| 9,063,239 B2* | 6/2015 | Oda | G01T 1/17 | |
| 9,101,316 B2* | 8/2015 | Liu | A61B 6/4233 | |
| 9,134,436 B2* | 9/2015 | Kwak | A61B 6/548 | |
| 9,158,004 B2* | 10/2015 | Oda | H04N 5/32 | |
| 9,168,011 B2* | 10/2015 | Nenoki | A61B 6/4233 | |
| 9,168,016 B2* | 10/2015 | Ohta | G01T 1/24 | |
| 9,192,350 B2* | 11/2015 | Hiroike | H05G 1/08 | |
| 9,194,964 B2* | 11/2015 | Ito | H04N 5/32 | |
| 9,204,855 B2* | 12/2015 | Tsubota | A61B 6/563 | |
| 9,216,006 B2* | 12/2015 | Kuwabara | A61B 6/4233 | |
| 9,258,464 B2* | 2/2016 | Ohta | H04N 5/321 | |
| 9,258,497 B2* | 2/2016 | Tsuji | H04N 5/32 | |
| 9,270,904 B2* | 2/2016 | Hammond | H05G 1/44 | |
| 9,282,943 B2* | 3/2016 | Oda | A61B 6/5258 | |
| 9,320,483 B2* | 4/2016 | Kobayashi | A61B 6/00 | |
| 9,335,422 B2* | 5/2016 | Oda | A61B 6/548 | |
| 9,402,592 B2* | 8/2016 | Garcia | A61B 6/4283 | |

(56) References Cited

U.S. PATENT DOCUMENTS

| | | | |
|---|---|---|---|
| 9,405,183 B2* | 8/2016 | Ando | A61B 6/4266 |
| 9,414,802 B2* | 8/2016 | Urbon | A61B 6/4283 |
| 9,462,982 B2* | 10/2016 | Suzuki | A61B 6/4283 |
| 9,492,137 B2* | 11/2016 | Iwamoto | A61B 6/563 |
| 9,513,379 B2* | 12/2016 | Nishino | A61B 6/548 |
| 9,521,983 B2* | 12/2016 | Jang | A61B 6/4429 |
| 9,521,986 B2* | 12/2016 | Ozawa | A61B 6/4283 |
| 9,535,176 B2* | 1/2017 | Miyoshi | G01T 7/00 |
| 9,538,978 B2* | 1/2017 | Makino | A61B 6/563 |
| 9,629,591 B2* | 4/2017 | Liu | A61B 6/4283 |
| 9,655,575 B2* | 5/2017 | Park | A61B 6/4233 |
| 9,668,706 B2* | 6/2017 | Kim | A61B 6/563 |
| 9,668,708 B2 | 6/2017 | Okuno et al. | |
| 9,675,309 B2 | 6/2017 | Kim | |
| 9,700,270 B2 | 7/2017 | Tateishi et al. | |
| 9,700,271 B2* | 7/2017 | Horiuchi | A61B 6/4405 |
| 9,700,278 B2* | 7/2017 | Tezuka | A61B 6/563 |
| 9,753,159 B2* | 9/2017 | Iwakiri | G01T 1/17 |
| 9,778,380 B2* | 10/2017 | Enomoto | G01T 1/161 |
| 9,810,001 B2* | 11/2017 | Bostley | E05B 65/006 |
| 9,833,214 B2* | 12/2017 | Imamura | A61B 6/586 |
| 9,855,017 B2 | 1/2018 | Wojcik et al. | |
| 9,955,931 B2 | 5/2018 | Bettouyashiki et al. | |
| 9,968,315 B2 | 5/2018 | Ogura et al. | |
| 2004/0066899 A1 | 4/2004 | Araki et al. | |
| 2006/0105819 A1 | 5/2006 | Liao | |
| 2009/0168970 A1 | 7/2009 | Xu et al. | |
| 2010/0303601 A1 | 12/2010 | Forcina | |
| 2012/0045037 A1 | 2/2012 | Carmichael et al. | |
| 2013/0064351 A1 | 3/2013 | Urbon et al. | |
| 2014/0016747 A1* | 1/2014 | Watanabe | A61B 6/56 378/62 |

OTHER PUBLICATIONS

Extended European Search Report dated Jan. 2, 2018, in corresponding European Patent Application No. 15843185.8, 7 pgs.
Office Action dated Jan. 7, 2019 in co-pending U.S. Appl. No. 15/857,289 (29 pages).

* cited by examiner

RECEIVING DEVICE AND X-RAY IMAGING APPARATUS HAVING THE SAME

CROSS-REFERENCE TO RELATED APPLICATION

This application claims the benefit of Korean Patent Application No. 10-2014-0127201, filed on Sep. 23, 2014 in the Korean Intellectual Property Office, the disclosure of which is incorporated herein by reference.

BACKGROUND

1. Field

Embodiments relate to a receiving device in which a detector is accommodated and an X-ray imaging apparatus having the same.

2. Description of the Related Art

An X-ray imaging apparatus is a non-invasive diagnostic apparatus that radiates X-rays to a subject, detects X-rays transmitted through the subject, and can image an internal structure of the subject.

Since general X-ray imaging apparatuses have an X-ray source and an X-ray detector, which are fixed in a certain space, a patient moves to a laboratory in which the X-ray imaging apparatus is positioned and moves his or her body to adjust to the apparatus in order to perform X-ray imaging.

However, since movement-impaired patients have difficulty in imaging using general X-ray imaging apparatuses, a mobile X-ray imaging apparatus capable of performing X-ray imaging at any place was developed.

The mobile X-ray imaging apparatus can perform X-ray imaging by directly visiting movement-impaired patients since an X-ray source is mounted in a movable main body and a portable X-ray detector is used.

The mobile X-ray imaging apparatus includes a receiving unit, and the portable X-ray detector may be accommodated in the receiving unit. For convenience of X-ray imaging, portable X-ray detectors of various sizes have been recently provided.

When a portable X-ray detector of a small size is accommodated in a receiving container that is provided according to a size of a portable X-ray detector of a large size, the portable X-ray detector may move in the receiving container when the mobile X-ray imaging apparatus is moved. Therefore, the portable X-ray detector comes in contact with an inner sidewall of the receiving container so that noise may be generated or the portable X-ray detector may be damaged.

In order to prevent the portable X-ray detector from being unstably accommodated in the receiving unit, the receiving unit of the mobile X-ray imaging apparatus may include the receiving container in which receiving units according to sizes of portable X-ray detectors having various sizes are provided to accommodate portable X-ray detectors of various sizes. In this case, since a size of the receiving unit in which the portable X-ray detector is accommodated increases, space utilization is limited.

SUMMARY

According to an embodiment, a receiving device in which detecting devices of various sizes can be stably accommodated in a receiving unit and an X-ray imaging apparatus having the same may be provided.

According to an aspect, there is provided a receiving device having a receiving unit in which a first detecting device is accommodated, the receiving device including: a fixing unit provided in the receiving unit and into which a part of a side surface of the first detecting device is inserted in order to prevent the first detecting device from being moved; and a detector support having a side that is connected to a rotating shaft and tiltable and configured to support at least one side surface of a second detecting device having a smaller size than the first detecting device.

An elastic member may be provided between the detector support and an inner side surface of the receiving unit, and the elastic member may provide an elastic force of pushing the detector support from the inner side surface of the receiving unit.

When the first detecting device is inserted into the receiving unit, the detector support may be pressed by the first detecting device and tilted to the inner side surface of the receiving unit.

A support bracket configured to support the elastic member may be provided behind the detector support.

The detector support may be rotatably mounted in a side support that is mounted in an inner side surface of the receiving unit.

When the second detector is inserted into the receiving unit, at least one side surface of the second detector may be supported by the side support.

The detector support may have a tilting angle that is restricted by a tilting restricting portion provided in the form of a groove or a hole in a side surface.

The tilting restricting portion may be provided to be a part of a concentric circle having the same center of rotation as a circle drawn by ends of the detector support.

The side support may include an intervention unit inserted into the tilting restricting portion.

The fixing unit may include a bottom fixing unit provided in a lower part of the receiving unit and configured to support a bottom of the first detecting device or a bottom of the second detecting device.

When the first detecting device or the second detecting device is mounted in the bottom fixing unit, the first detecting device or the second detecting device may be charged.

The fixing unit may include a side fixing unit having an insertion groove into which parts of both side surfaces of the first detecting device are inserted.

The side fixing unit may be provided in the left and right sides of the receiving unit.

A rail unit may be provided in an inner side surface of the receiving unit, and the detector support may be movable along the rail unit.

A plurality of the detector supports may be provided.

According to another aspect, there is provided an X-ray imaging apparatus, including: a movable main body; an X-ray generating unit mounted in the main body and configured to generate X-rays; a detecting device configured to detect X-rays generated from the X-ray generating unit; a receiving device mounted in the main body and having a receiving unit in which the detecting device is accommodated; and a detector support configured to support a side surface of a detecting device having a smaller horizontal length than the receiving unit.

The detector support may be tiltable with respect to a rotation axis.

An elastic member may be provided between the detector support and an inner side surface of the receiving unit.

The elastic member may have a directional elastic force that increases a distance between the detector support and the inner side surface of the receiving unit.

When a detecting device having a horizontal length corresponding to a horizontal length of the receiving unit is inserted into the receiving unit, the detector support may be pressed by the detecting device, and a distance between the detector support and an inner side surface of the receiving unit may decrease.

The detector support may be tiltably mounted in a body unit in which a receiving unit in which the detector support is able to be accommodated is formed.

The receiving unit may have left and right inner sides having a side fixing unit into which a part of at least one side surface of the detecting device is inserted and fixed.

The receiving unit may have a lower part including a bottom fixing unit in which a mounting groove in which the detecting device is mounted and fixed is formed.

When the detecting device is mounted in the bottom fixing unit, the detecting device may be charged.

The receiving device may include a rail unit that horizontally extends, and the detector support may be movable along the rail unit.

The rail unit may further include a stopper configured to restrict movement of the detector support.

A plurality of the detector supports may be provided.

The plurality of detector supports may be movable along a rail unit provided in the receiving device.

According to another aspect, there is provided an X-ray machine including an X-ray generator and a portable X-ray detector receiver stably holding a portable X-ray detector as the machine is moved by applying a stabilizing force to one of or both of a side of each detector and an edge of each detector. The may include a stabilization arm to apply one of pressure to the side of the detector and to contact a side edge of the detector responsive to a length to the detector. The receiver may further include a pair of grooves into which the detector may slide. The receiver may further include a support on an opposite side of the detector against which the detector is pushed by the stabilization arm. The receiver may also include a bottom support channel to hold a lower edge of the detector. The stabilization arm may include a pivot arm to pivot to apply the pressure and to be positioned to provide the contact. The stabilization arm may further include a spring pushing the pivot arm. The pivot arm may include a groove with ends and a pin to slide in the groove and contact the ends to limit pivoting. The receiver may further include a rail along which one or more stabilization arms slide to adjust to different size detectors.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Hereinafter, a receiving device according to an embodiment and an X-ray imaging apparatus having the same will be described in detail with reference to the drawings.

Figure 1:
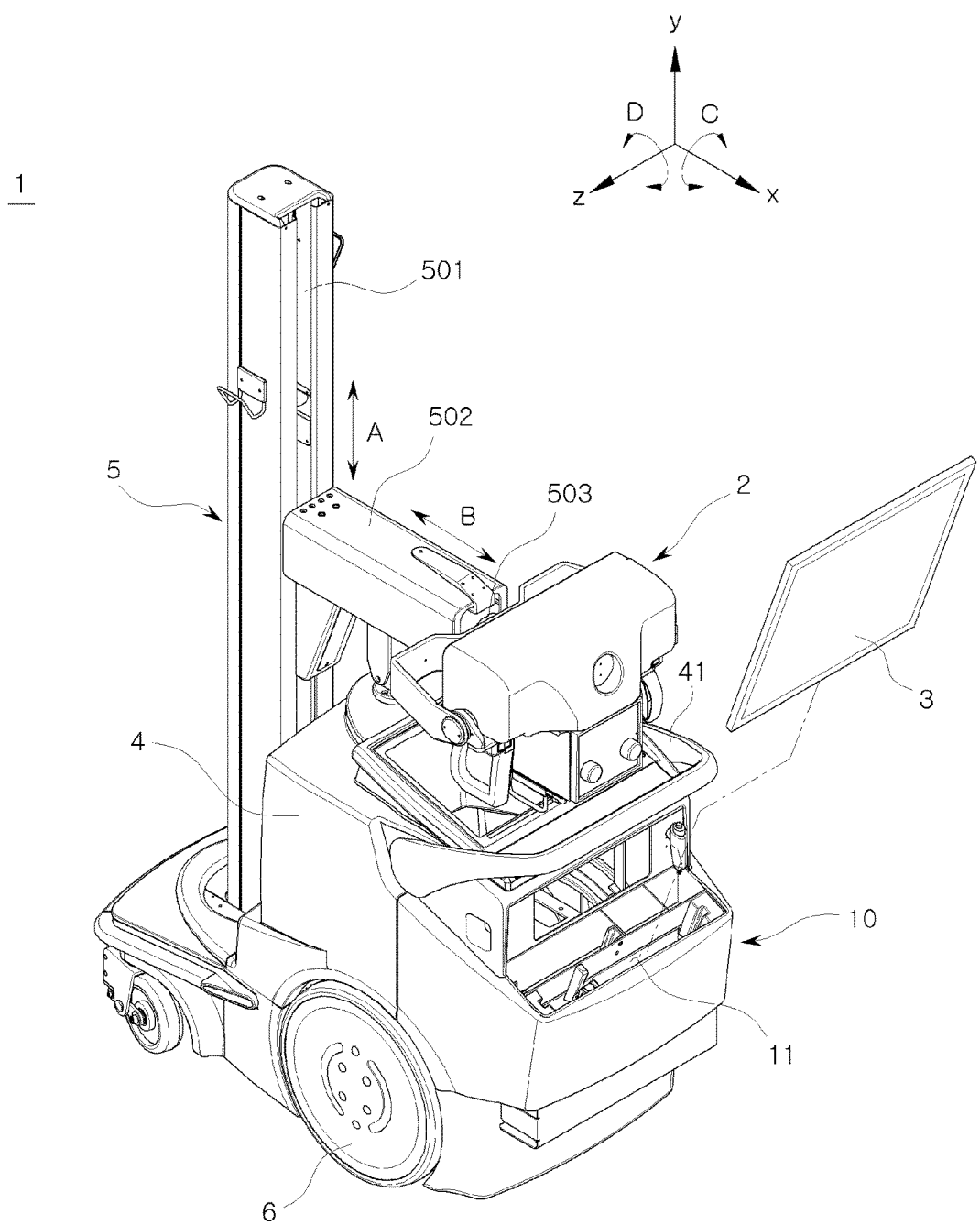
FIG. 1 is a diagram illustrating a mobile X-ray imaging apparatus according to an embodiment.

FIG. 1 is a diagram illustrating a mobile X-ray imaging apparatus according to an embodiment.

As illustrated in FIG. 1, a mobile X-ray imaging apparatus 1 according to the embodiment may include an X-ray generating unit 2 and a detecting device 3. The X-ray generating unit 2 may be mounted in a main body 4, and the detecting device 3 may be accommodated in a receiving device 10 provided in the main body 4. The main body 4 is movable by a caster 6. The main body 4 includes a handgrip 41. A user may move the main body 4 by grasping and pushing or pulling the handgrip 41.

The X-ray generating unit 2 may receive a driving force from a driving unit (not illustrated) provided in the main body 4 and generate X-rays. X-ray energy may be controlled by a tube voltage. An intensity of a dose of X-rays may be controlled by a tube current and an X-ray exposure time.

The X-ray generating unit 2 is movable together with the main body 4. The main body 4 may include a moving unit 5. The moving unit 5 may include a first guide rail 501 and a second guide rail 502. The first guide rail 501 and the second guide rail 502 may be installed to form a predetermined angle.

As an example, the first guide rail 501 may be perpendicular to the second guide rail 502. The first guide rail 501 may vertically extend from a bottom surface on which the main body 4 is mounted. The second guide rail 502 may horizontally extend from the bottom surface on which the main body 4 is mounted. The second guide rail 502 is movable along the first guide rail 501. The first guide rail 501 may extend in a y axis direction, the second guide rail 502 may extend in an x axis direction, and the second guide rail 502 is movable in a vertical direction (direction A) along the y axis.

The X-ray generating unit 2 may be mounted in the second guide rail 502. The X-ray generating unit 2 is movable in a direction in which the second guide rail 502 extends. That is, the X-ray generating unit 2 is movable in a direction (direction B) that is horizontal to the bottom surface along the x axis.

Also, the X-ray generating unit 2 is rotatable about the x axis or a z axis. The X-ray generating unit 2 is connected to the second guide rail 502 by a rotary joint 503 that is rotatable, and may rotate (direction C) about the x axis or rotate (direction D) about the z axis by a rotary joint 503.

A position and an angle of rotation of the X-ray generating unit 2 may be regulated by the moving unit 5 and the rotary joint 503 according to a position of a subject to be imaged using X-rays.

The main body 4 may include a driving unit configured to regulate the position and angle of rotation of the X-ray generating unit 2. The driving unit may be a motor that is electrically driven.

A manipulating unit configured to input various pieces of information about X-ray imaging and manipulate respective devices may be provided at a side of the main body 4.

A mobile detecting device 3 may be provided. The detecting device 3 may be accommodated in a receiving unit 11 of the receiving device 10 that is provided in the main body 4. The detecting device 3 may be moved to a position at which X-ray imaging is required along with the main body 4. When X-ray imaging is required, the user may withdraw the detecting device 3 from the receiving device 10, enable the detecting device 3 to be positioned behind the subject to be imaged using X-rays, and perform X-ray imaging.

The detecting device 3 may include a detector and a grid. The detector may detect X-rays that pass through the subject and convert the X-rays into an electrical signal. X-ray data of the subject may be obtained by the detector. The grid may be positioned in front of the detector to block scattered rays of X-rays generated from the X-ray generating unit 2.

The detecting device 3 may be fixed not to move in the receiving unit 11 provided in the receiving device 10. The receiving unit 11 may be provided according to a size of the detecting device 3 and fix at least one side of the detecting device 3. Therefore, it is possible to prevent the detecting device 3 from moving in the receiving unit 11, colliding with an inner side surface of the receiving device 10 forming the receiving unit 11, and generating noise, or prevent the detecting device 3 from being damaged.

The detecting device 3 may have a substantially rectangular shape. A shape of the detecting device 3 is not limited to the rectangular shape. However, the detecting device 3 will be described below as having a rectangular shape.

When X-ray imaging is performed, the detecting device 3 of a different size may be used as necessary. For example, the detecting device 3 of a large or small size may be used according to an area of the subject to be imaged using X-rays. The detecting device 3 having a square shape may be used, or the detecting device 3 having a rectangular shape whose horizontal length is greater than a vertical length may be used.

If the receiving unit 11 provided in the receiving device 10 is provided according to a size of the biggest detecting device 3, when a detecting device having a smaller size than the biggest detecting device 3 is inserted into the receiving unit, the detecting device may collide with an inner side surface of the receiving device forming the receiving unit according to movement of the main body 4, and the detecting device may be damaged, or clattering noise may be generated.

In order to accommodate and fix the detecting devices 3 of different sizes not to move, a structure in which receiving units of various sizes are provided in the receiving device to correspond to various sizes of detecting devices may be considered. In this case, since a plurality of receiving units of different sizes need to be provided in the receiving device, space utilization may be limited.

Hereinafter, the receiving device 10 in which detecting devices of different sizes can be stably accommodated without constraints on space utilization of the receiving device 10 will be described.

Figure 2:
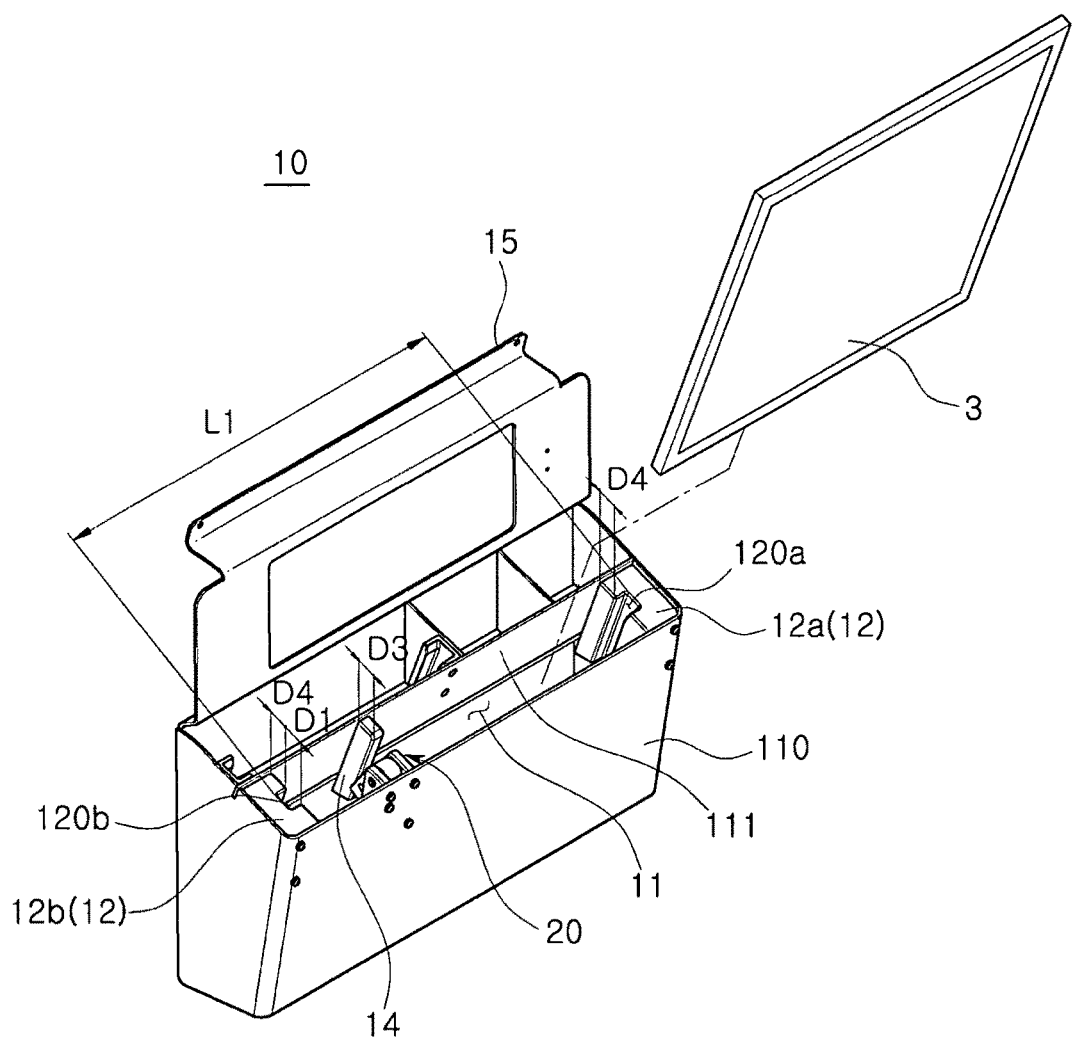
FIG. 2 is a perspective view of a receiving device according to an embodiment.
Figure 3:
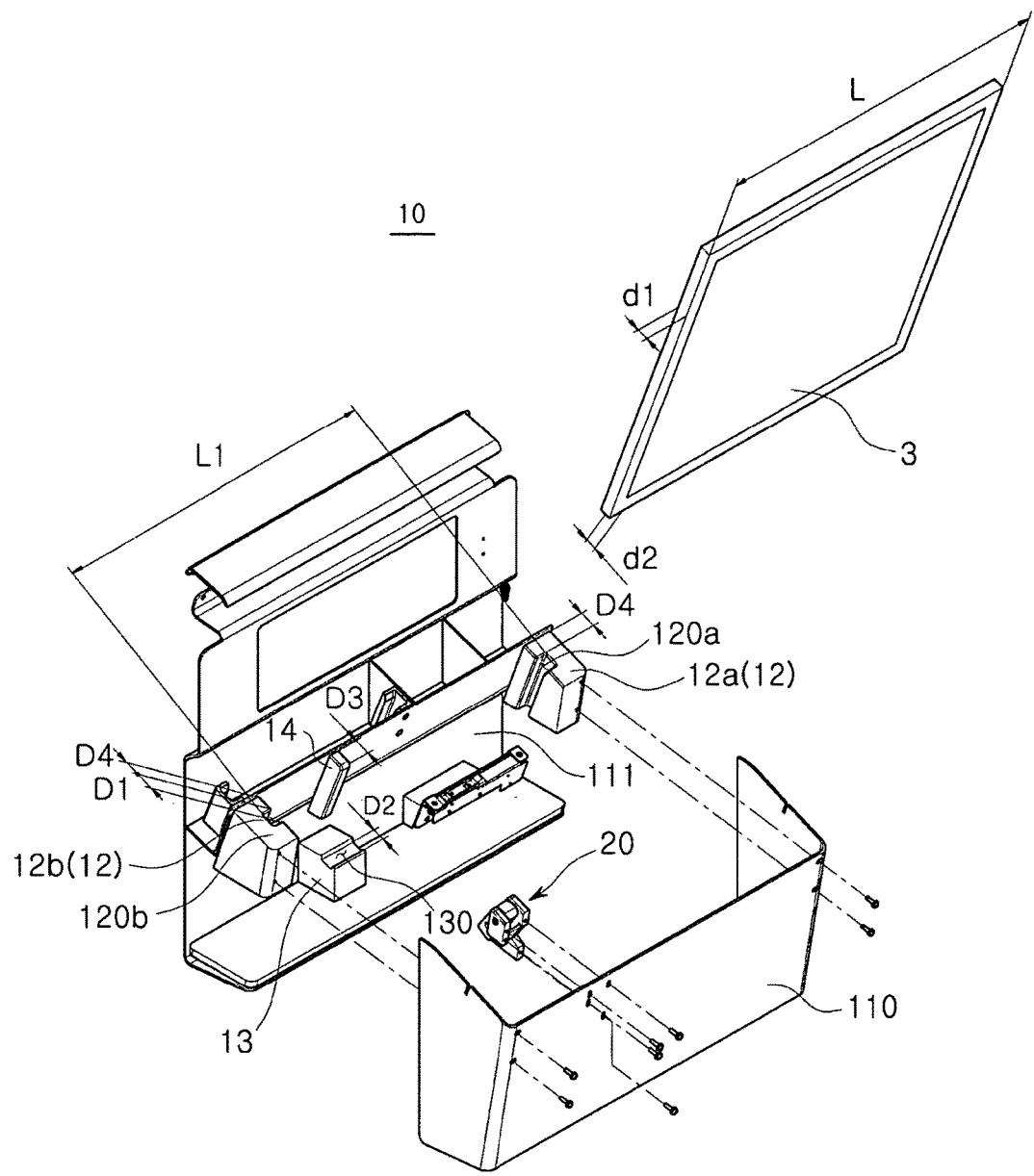
FIG. 3 is a diagram illustrating a configuration of a receiving device according to an embodiment.
Figure 4:
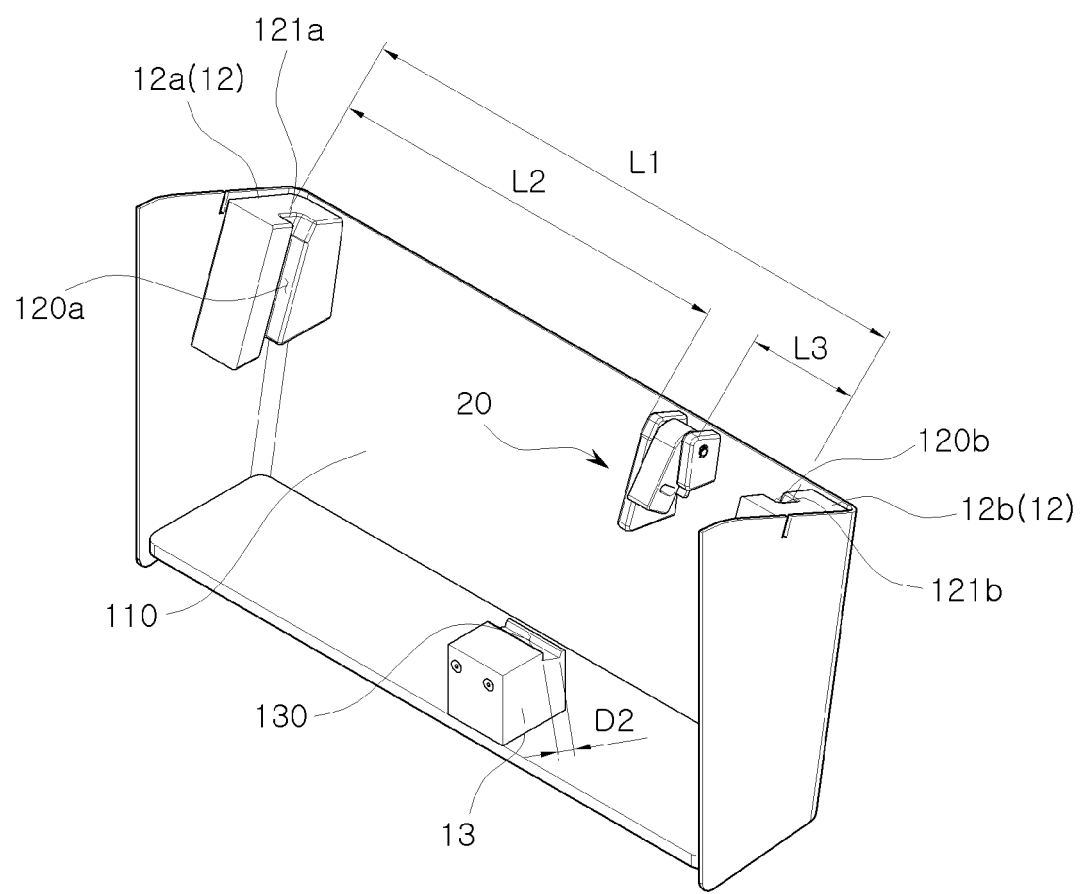
FIG. 4 is a diagram illustrating a state in which a guide unit is mounted in a receiving device according to an embodiment.

FIG. 2 is a perspective view of a receiving device according to an embodiment. FIG. 3 is a diagram illustrating a configuration of a receiving device according to an embodiment. FIG. 4 is a diagram illustrating a state in which a guide unit is mounted in a receiving device according to an embodiment.

As illustrated in FIGS. 2 to 4, the receiving device 10 according to the embodiment may include the receiving unit 11 in which the detecting device 3 can be accommodated. The receiving unit 11 may be formed to correspond to the size of the biggest detecting device among detecting devices of various sizes that can be used when X-ray imaging is performed.

A flange portion 15 may be formed at a side of the receiving device 10. The receiving device 10 may be combined with the main body 4 by the flange portion 15 and a fastening member penetrating through a side of the main body 4. A method in which the receiving device 10 is mounted in the main body 4 is not limited to the above. The receiving device 10 may be fixed to the main body 4 and detachable from the main body 4.

Fixing units 12 and 13 into which a part of the detecting device 3 can be inserted and fixed may be provided in the receiving unit 11. The fixing units 12 and 13 may include the side fixing unit 12 into which parts of the left and right sides of the detecting device 3 can be inserted and fixed and the bottom fixing unit 13 configured to support a bottom surface of the detecting device 3.

The side fixing unit 12 may include a first side fixing unit 12a and a second side fixing unit 12b which are provided in the left and right sides of the receiving unit 11, respectively. A first insertion groove 120a and a second insertion groove 120b into which parts of the left and right sides of the detecting device 3 can be inserted may be provided in the first side fixing unit 12a and the second side fixing unit 12b. Widths D1 of the first insertion groove 120a and the second insertion groove 120b may correspond to a width d1 of a side surface of the detecting device 3.

A part of a side surface of the detecting device 3 may be inserted into and fixed to the first insertion groove 120a and the second insertion groove 120b. The first insertion groove 120a and the second insertion groove 120b may extend in a vertical direction such that the part of the side surface of the detecting device 3 may be slidably inserted.

A length L1 from one surface 121a of the first insertion groove 120a to one surface 121b of the second insertion groove 120b may correspond to a horizontal length of a detecting device having the greatest horizontal length among detecting devices of various sizes that can be used when X-ray imaging is performed. The detecting device having the greatest horizontal length may slide in a longitudinal direction of the first insertion groove 120a and the second insertion groove 120b when a part of a left side of the detecting device 3 is inserted into the first insertion groove 120a and a part of a right side of the detecting device 3 is inserted into the second insertion groove 120b. Therefore, the detecting device may be accommodated in the receiving unit 11, inserted into the first insertion groove 120a and the second insertion groove 120b, and the left and right sides may be fixed not to move.

The bottom fixing unit 13 may include a mounting unit 130 on which a bottom of the detecting device 3 may be mounted. A part of the bottom of the detecting device 3 may be inserted into the mounting unit 130. A part of the bottom of the detecting device 3 may be inserted into the mounting unit 130 and fixed not to move. A width D2 of the mounting unit 130 may correspond to a width d2 of the bottom of the detecting device 3.

The bottom fixing unit 13 may include a charging terminal 13a capable of charging the detecting device 3. As an example, the charging terminal 13a may be provided in the mounting unit 130 on which the bottom of the detecting device 3 is mounted. When the detecting device 3 is accommodated in the receiving unit 11, a charging terminal 9 provided in the detecting device 3 and the charging terminal 13a provided in the bottom fixing unit 13 are connected to perform charging.

A support 14 capable of supporting a rear surface of the detecting device 3 may be provided in the inner side surface of the receiving device 10 forming the receiving unit 11. The support 14 may be provided in at least one of an inner front surface 110 and an inner rear surface 111 of the receiving device 10 forming the receiving unit 11.

A length D3 by which the support 14 protrudes forward may correspond to a length D4 from the inner rear surface 111 of the receiving device 10 to the first insertion groove 120a and the second insertion groove 120b of the side fixing units 12a and 12b provided at each side of the receiving unit 11. When the left and right sides of the detecting device 3 are inserted into the first insertion groove 120a and the second insertion groove 120b, the rear surface of the detecting device 3 may be supported by the support 14. Therefore, the detecting device 3 may be stably accommodated in the receiving unit 11.

A guide unit 20 may be provided in the inner side surface of the receiving device 10 forming the receiving unit 11. The guide unit 20 may be provided in at least one of the inner front surface 110 and the inner rear surface 111 of the receiving device 10 forming the receiving unit 11. Hereinafter, a case in which the guide unit 20 is provided in the inner front surface 110 of the receiving device 10 will be described.

The guide unit 20 includes a first side portion 21 and a second side portion 22 which are disposed to face each other with a predetermined interval therebetween. A detector support 23 configured to rotate a predetermined angle with respect to a rotation axis may be provided between the first side portion 21 and the second side portion 22.

The guide unit 20 may support a front surface of the detecting device 3 or a side surface of the detecting device 3. When a horizontal length L of the detecting device 3 is the same as a length L1 from the one surface 121a of the first insertion groove 120a formed in the first side fixing unit 12a to the one surface 121b of the second side fixing unit 12b, the guide unit 20 may support the front surface of the detecting device 3.

When a length from the one surface 121a of the first insertion groove 120a to the first side portion 21 of the guide unit 20 is set to L2, and a length from the second side portion 22 of the guide unit 20 to the one surface 121b of the second insertion groove 120b is set to L3, a one-side surface of the detecting device 3 whose horizontal length is L2 comes in contact with the one surface 121a of the first insertion groove 120a, and the other-side surface may be inserted into the receiving unit 11 to come in contact with the first side portion 21 of the guide unit 20. The detecting device 3 whose horizontal length is L2 may be fixed not to move inside the receiving unit 11 when a right-side surface is inserted into and fixed to the first insertion groove 120a, and a left-side surface is supported by the first side portion 21 of the guide unit 20.

Also, the detecting device 3 whose horizontal length is L3 may be inserted into the receiving unit 11 such that a one-side surface thereof comes in contact with the one surface 121b of the second insertion groove 120b, and the other-side surface thereof comes in contact with the second side portion 22 of the guide unit 20. The detecting device 3 whose horizontal length is L3 may be fixed not to move inside the receiving unit 11 when a right-side surface is supported by the second side portion 22 of the guide unit 20 and a left-side surface is inserted into and fixed to the second insertion groove 120b.

Hereinafter, a detailed configuration of the guide unit 20 will be described in detail with reference to the drawings.

Figure 5:
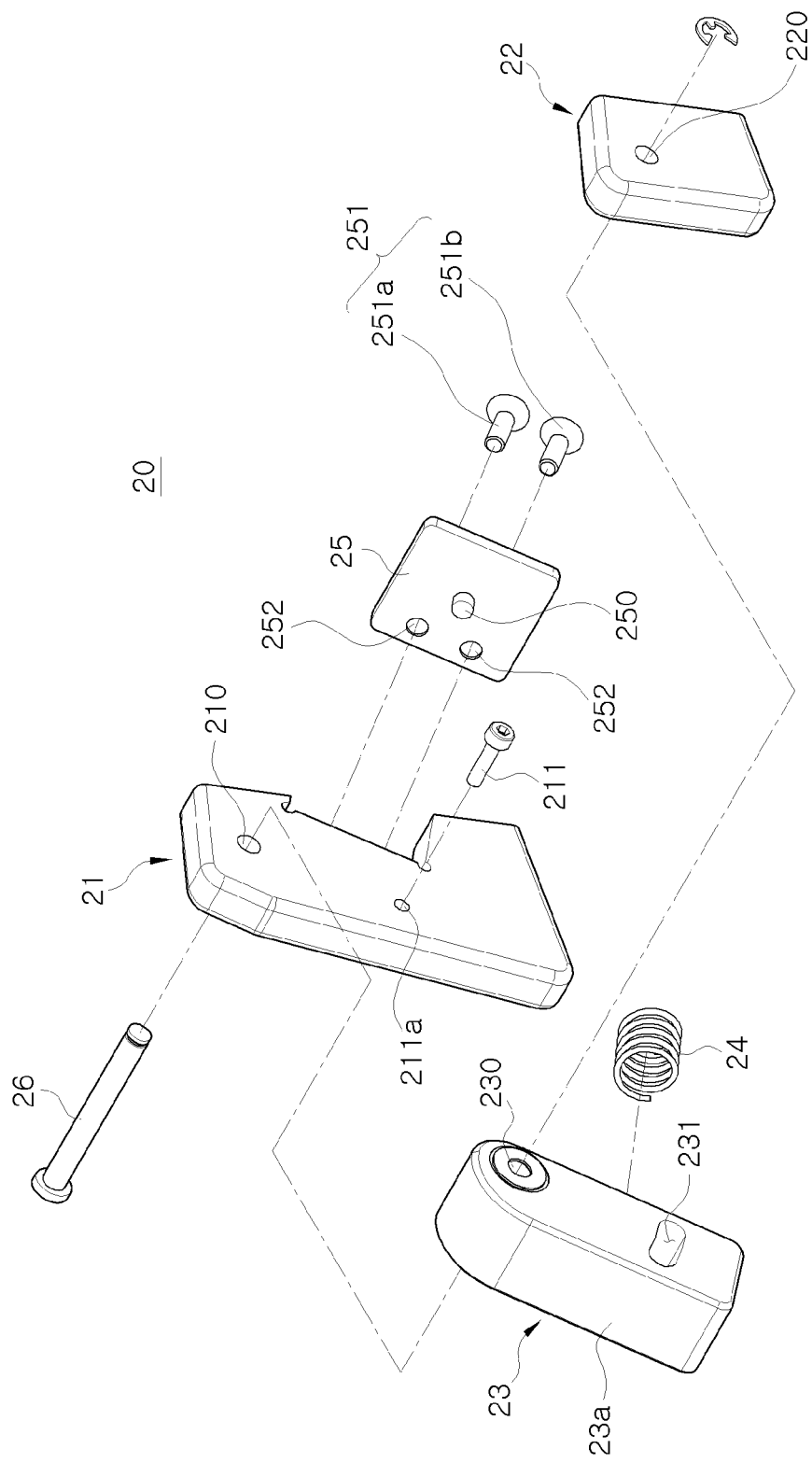
FIG. 5 is an exploded perspective view of a guide unit according to an embodiment.
Figure 6:
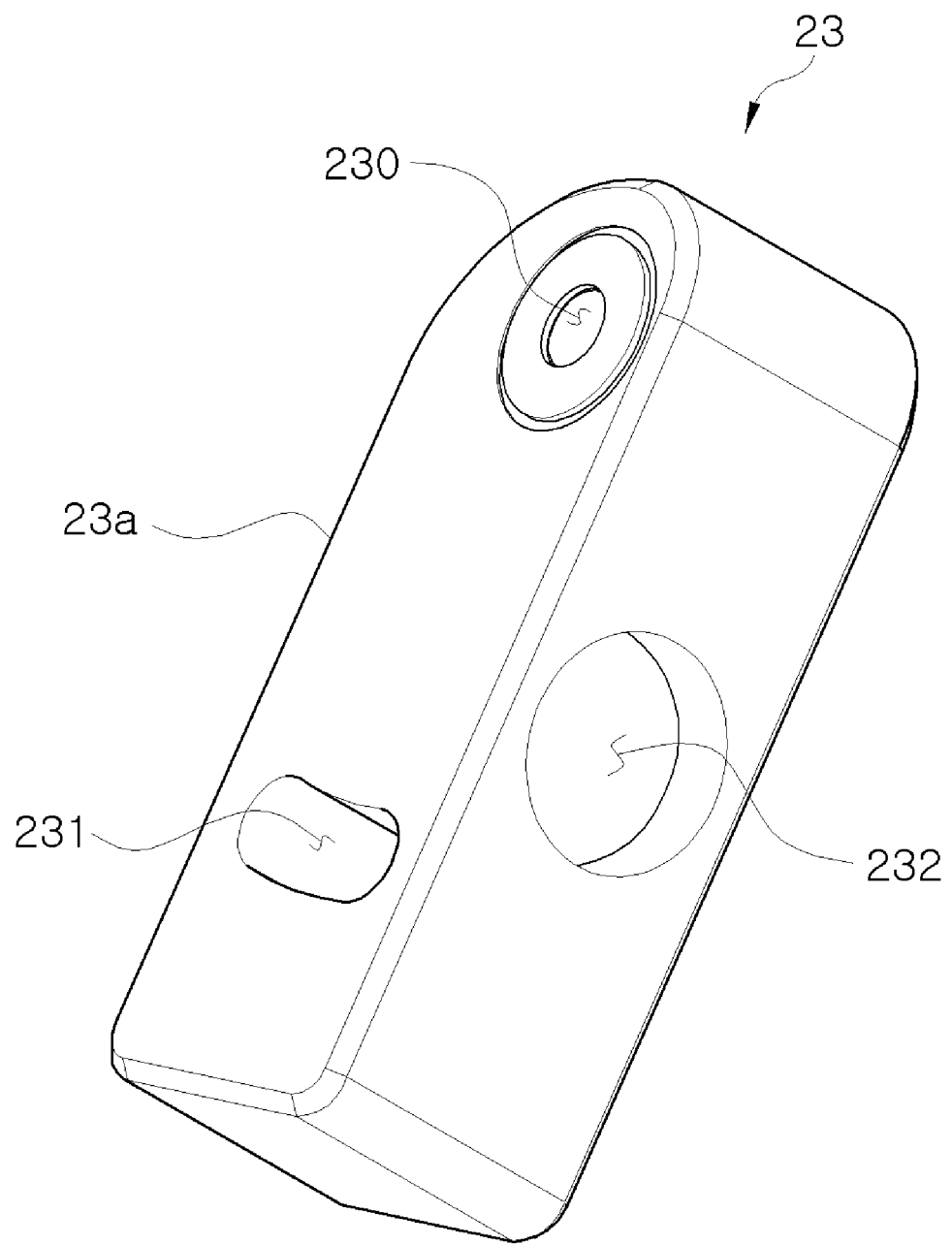
FIG. 6 is a diagram illustrating a detector guide according to an embodiment.

FIG. 5 is an exploded perspective view of a guide unit according to an embodiment. FIG. 6 is a diagram illustrating a detector guide according to an embodiment.

As illustrated in FIGS. 5 and 6, the guide unit 20 according to the embodiment includes the detector support 23 that is pivotally mounted on the inner side surface of the receiving device 10. The detector support 23 may be mounted on the inner side surface of the receiving device 10 by the first side portion 21 and the second side portion 22. The first side portion 21 and the second side portion 22 may be disposed to face each other with a predetermined interval therebetween and fixed to the inner side surface of the receiving device 10.

The detector support 23 may be positioned between the first side portion 21 and the second side portion 22. The detector support 23 may be pivotally mounted on the first side portion 21 and the second side portion 22 by a rotating shaft 26. The rotating shaft 26 may pass through a rotating shaft insertion hole 210 formed in the first side portion 21, a rotating shaft insertion hole 230 formed at a side of the detector support 23, and a rotating shaft insertion hole 220 formed in the second side portion 22. The detector support 23 may be pivoted about the rotating shaft 26.

An elastic member 24 may be provided between one surface of the detector support 23 and the inner front surface 110 of the receiving device 10. The elastic member 24 may provide an elastic force such that the detector support 23 faces the inner rear surface 111 of the receiving device 10. That is, the elastic member 24 may provide an elastic force of pushing the detector support 23 from the inner front surface 110 to the detector support 23. The elastic member 24 may be a spiral spring.

The receiving device 10 may include a support bracket 25 configured to support the elastic member 24. The support bracket 25 may be positioned between the detector support 23 and the inner front surface 110 of the receiving device 10. The support bracket 25 may be mounted on at least one of the first side portion 21 and the second side portion 22. When the detector support 23 is pressed by the detecting device 3 that is inserted into the receiving unit 11, the elastic member 24 may be compressed between the detector support 23 and the support bracket 25.

The support bracket 25 may include an elastic member fixing unit 250. As an example, the elastic member fixing unit 250 may protrude from one surface of the support bracket 25, and the elastic member 24 may be mounted in the elastic member fixing unit 250.

The detector support 23 may include an elastic member insertion groove 232 into which the elastic member 24 can be inserted. The elastic member 24 has a position that is fixed by the elastic member fixing unit 250 of the support bracket 25, is inserted into the elastic member insertion groove 232, and can press the other side of the detector support 23 backward.

A tilting restricting portion 231 may be provided in a side portion of the detector support 23. The tilting restricting portion 231 may be provided in the form of a groove or a hole having a predetermined length. An intervention unit 211 that can be inserted into the tilting restricting portion 231 may be provided in any of the first side portion 21 and the second side portion 22. FIG. 5 illustrates an embodiment in which an intervention hole 211a into which the intervention unit 211 can be inserted is formed in the first side portion 21, and the intervention unit 211 is inserted into and fixed to the intervention hole 211a. A configuration of the intervention unit 211 is not limited to the above. The intervention unit 211 may protrude from the first side portion 21 together with the first side portion 21.

The intervention unit 211 is inserted into the tilting restricting portion 231, and may restrict an angle at which the detector support 23 tilts forward or backward. In this case, the tilting restricting portion 231 may be formed to be a part of a concentric circle having the same center of rotation as a circle drawn by ends of the detector support 23 when the detector support 23 rotates about the rotating shaft 26.

Hereinafter, an operation of the guide unit 20 when the detecting device 3 of a different size is inserted into the receiving unit 11 will be described.

Figure 7:
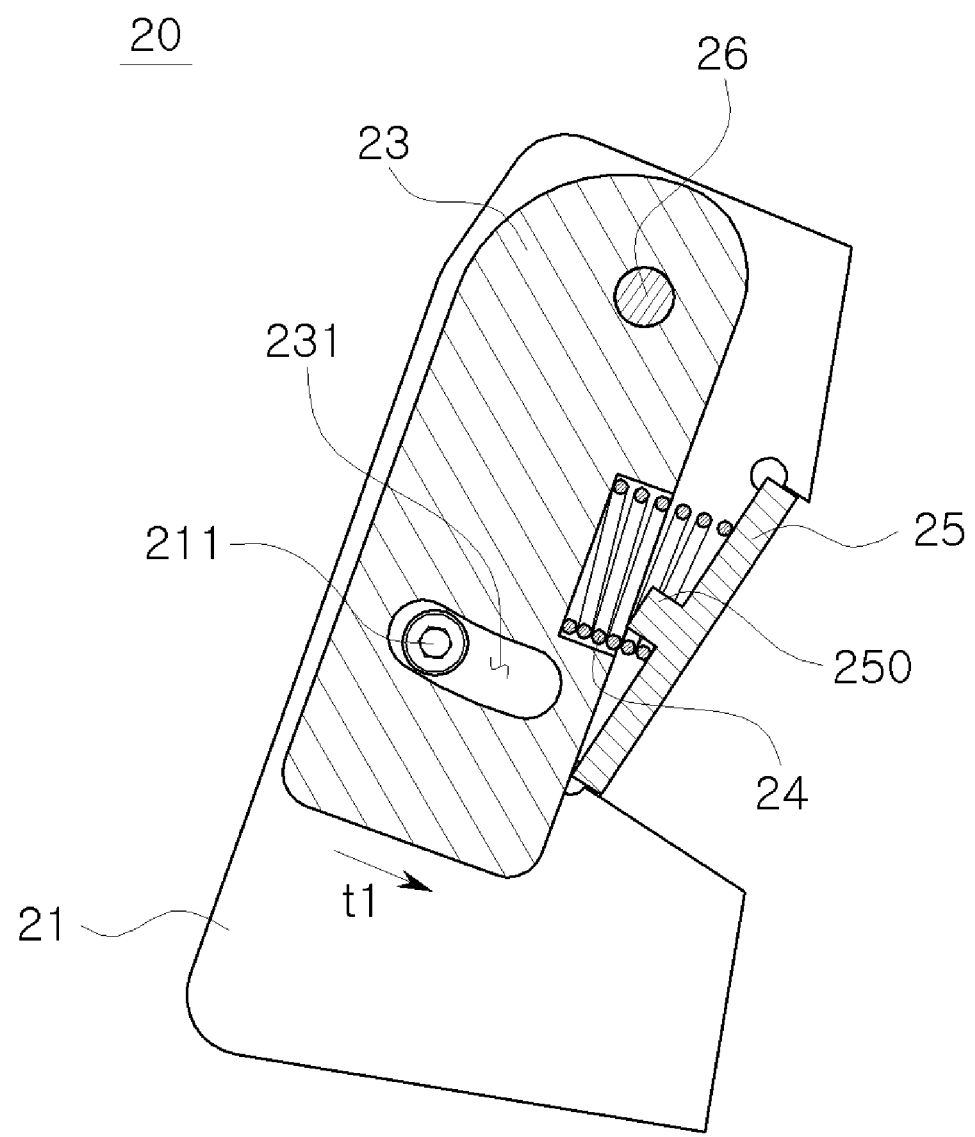
FIG. 7 is a side view of a guide unit when a detector guide according to an embodiment is in a first position.
Figure 8:
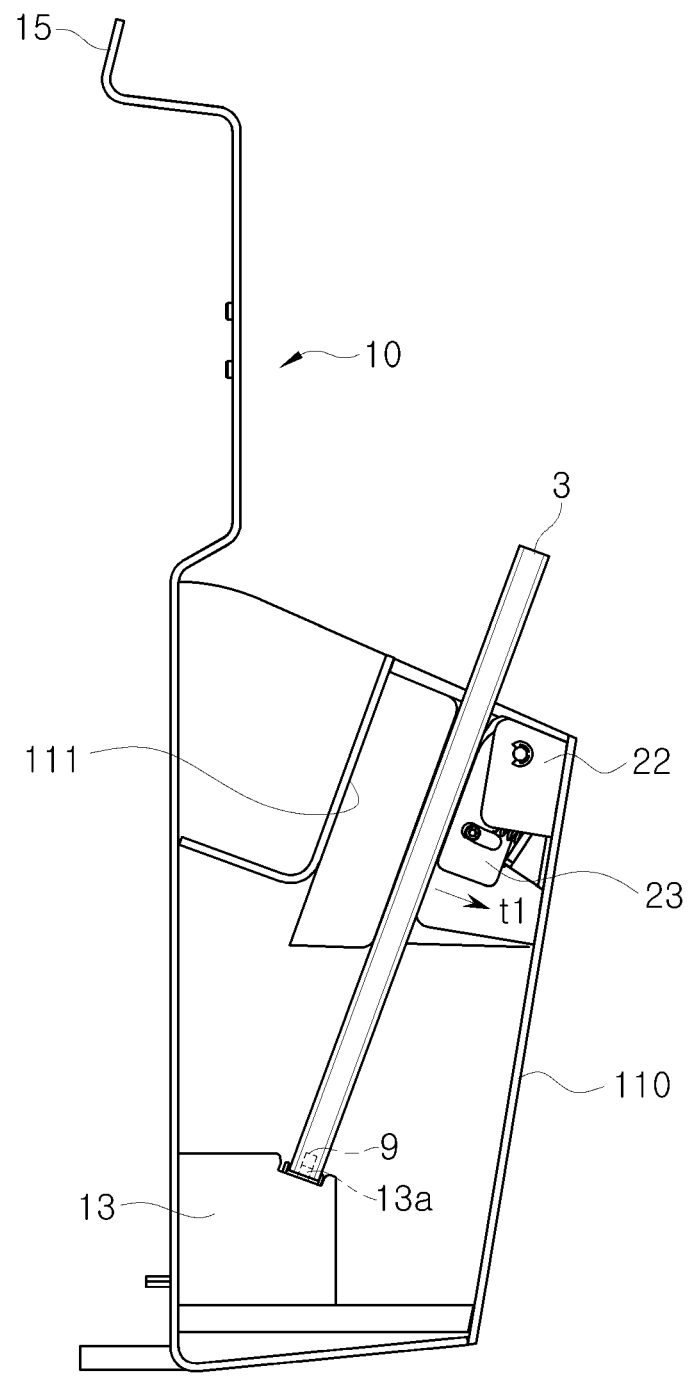
FIG. 8 is a side view of a receiving device when a detector guide according to an embodiment is in a first position.

FIG. 7 is a side view of a guide unit when a detector guide according to an embodiment is in a first position. FIG. 8 is a side view of a receiving device when a detector guide according to an embodiment is in a first position.

As illustrated in FIGS. 7 and 8, when the detecting device 3 is inserted into the receiving device 10 according to the embodiment, the detector support 23 may be tilted forward (direction t1: refer to FIG. 7) by the detecting device 3. In this case, a length L by which the detecting device 3 horizontally extends may correspond to a length L1 from the one surface 121a of the first insertion groove 120a to the one surface 121b of the second insertion groove 120b of the side fixing unit 12 provided in the receiving device 10.

In the detecting device 3, a part of a side surface of the detecting device 3 may be slidably inserted into the first insertion groove 120a and the second insertion groove 120b formed in the first side fixing unit 12a and the second side fixing unit 12b. In the detector support 23, one side is tiltable by the rotating shaft 26 and the other side may face behind the receiving device 10 due to an elastic force of the elastic member 24. The other side of the detector support 23 may be tilted at a predetermined angle by the tilting restricting portion 231 and the intervention unit 211 and then stopped. The other side of the detector support 23 may come in contact with the inner rear surface 111 of the receiving device 10 forming the receiving unit 11.

The detecting device 3 may slide along the first insertion groove 120a and the second insertion groove 120b formed in the first side fixing unit 12a and the second side fixing unit 12b, and may push and slide the detector support 23 when the detecting device 3 comes in contact with one surface 23a of the detector support 23. The detector support 23 may be tilted in the direction t1 with respect to the rotating shaft 26, and the other side of the detector support 23 may face the front surface 110 of the receiving device 10. When the detector support 23 is tilted in the direction t1, the elastic member 24 may be compressed between the detector support 23 and the front surface 110 of the receiving device 10. The elastic member 24 can press the support bracket 25. The other side of the detector support 23 may support one surface of the detecting device 3 such that the detecting device 3 can be stably accommodated in the receiving unit 11.

In this manner, when the detecting device 3 having a horizontally extending length L that corresponds to a length L1 from the one surface 121a of the first insertion groove 120a to the one surface 121b of the second insertion groove 120b of the side fixing unit 12 provided in the receiving device 10 is inserted into the receiving unit 11, the detector support 23 may be tilted by the detecting device 3 not to interfere with movement of the detecting device 3.

The detecting device 3 may be accommodated in the receiving unit 11 when a front surface comes in contact with the detector support 23, a rear surface comes in contact with the support 14, and parts of both side surfaces are inserted into the first insertion groove 120a and the second insertion groove 120b.

Hereinafter, a case in which the detecting device 3 whose horizontally extending length is L that is the same as a length L2 from the one surface 121a of the first insertion groove 120a to the first side portion 21 of the guide unit 20 is stably accommodated in the receiving unit 11 of the receiving device 10 will be described.

Figure 9:
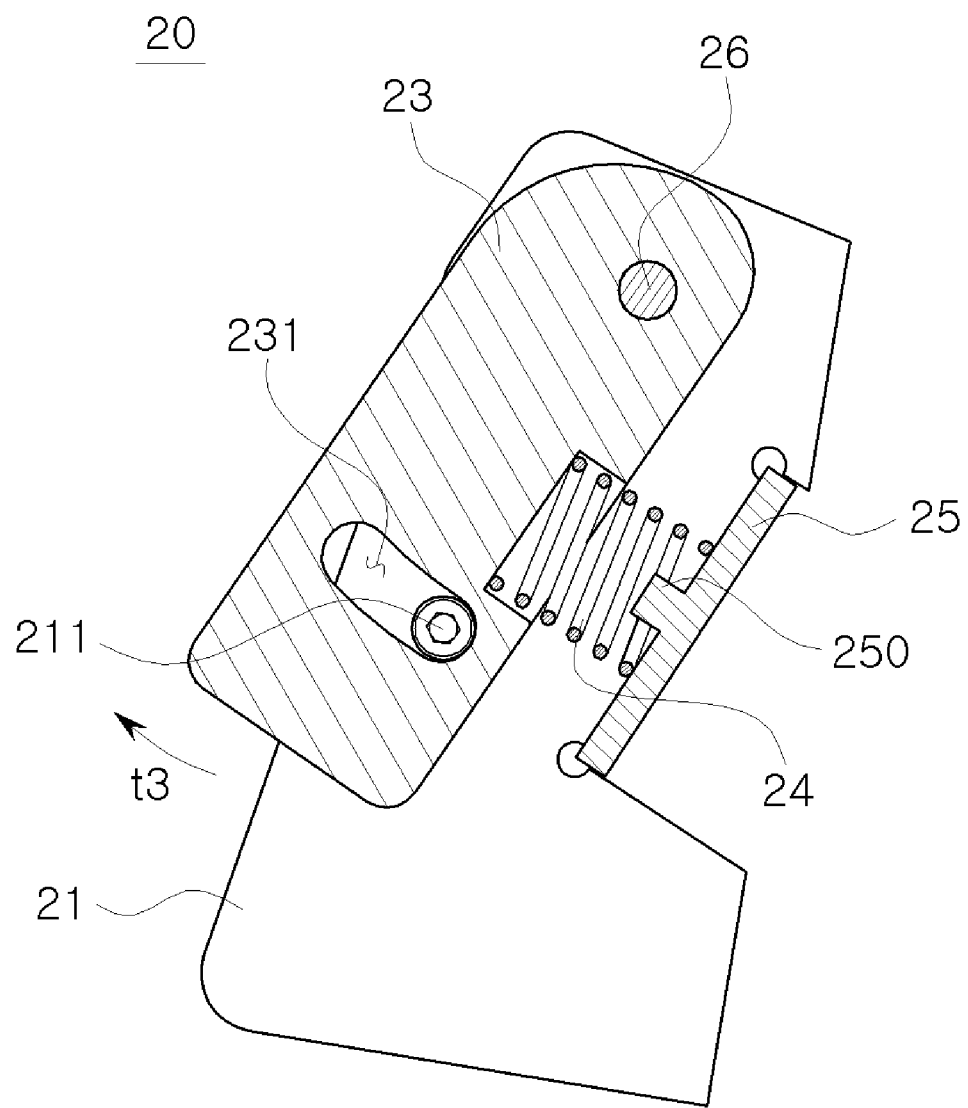
FIG. 9 is a side view of a guide unit when a detector guide according to an embodiment is in a second position.
Figure 10:
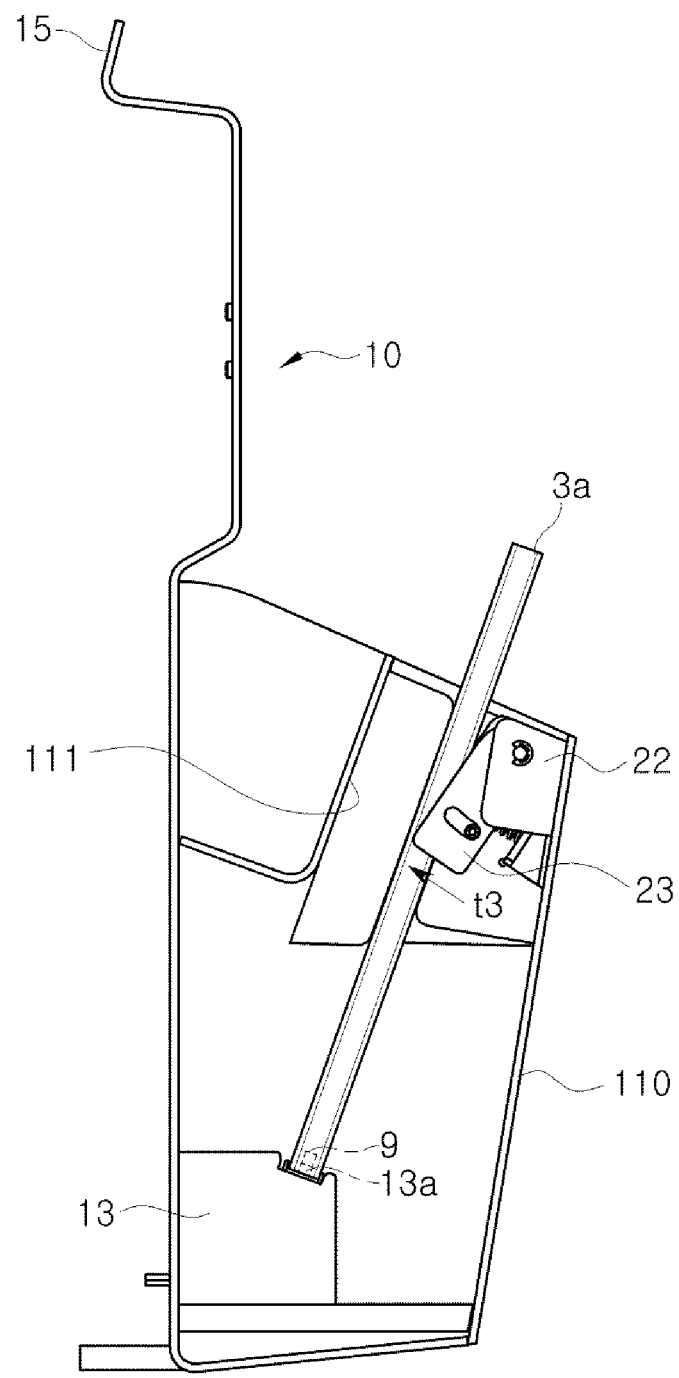
FIG. 10 is a side view of a receiving device when a detector guide according to an embodiment is in a second position.

FIG. 9 is a side view of a guide unit when a detector guide according to an embodiment is in a second position. FIG. 10 is a side view of a receiving device when a detector guide according to an embodiment is in a second position.

As illustrated in FIGS. 9 and 10, a horizontally extending length L of the detecting device 3 according to the embodiment may be any of a length L2 from the one surface 121a of the first insertion groove 120a of the side fixing unit 12 to the first side portion 21 of the guide unit 20 and a length L3 from the one surface 121b of the second insertion groove 120b of the side fixing unit 12 to the second side portion 22 of the guide unit 20. Hereinafter, the horizontally extending length L of the detecting device 3 will be described as the length L2 from the one surface 121a of the first insertion groove 120a of the side fixing unit 12 to the first side portion 21 of the guide unit 20.

Meanwhile, when the detecting device 3 whose horizontally extending length L corresponds to the length L1 from the one surface 121a of the first insertion groove 120a to the one surface 121b of the second insertion groove 120b of the side fixing unit 12 provided in the receiving device 10 is removed from the receiving unit 11, a force pressing the detector support 23 is removed, and the other side of the detector support 23 may be tilted to face behind the receiving device 10 due to the elastic force of the elastic member 24. That is, the detector support 23 may rotate in a direction t3 that is a direction opposite to the direction t1 with respect to the rotating shaft 26.

The detector support 23 has a tilting angle that may be restricted by the intervention unit 211 inserted into the tilting restricting portion 231. The detector support 23 may be tilted at a maximum tilt angle by the tilting restricting portion 231 and the intervention unit 211 and then stopped. Meanwhile, the detector support 23 may be tilted until the other side thereof comes in contact with an inner rear surface of the receiving device forming the receiving unit 11.

When the detector support 23 is tilted in the direction t3, the elastic member 24 positioned between the detector support 23 and the support bracket 25 can expand. At least a part of the elastic force stored in the contracted elastic member 24 is used to tilt the detector support 23. When the detector support 23 is tilted at a predetermined angle, the elastic member 24 may expand and have an elastic force smaller than that before the detector support 23 is tilted.

When the detecting device 3 whose horizontally extending length is L1 is removed from the receiving unit 11, a first section (length: L) from the one surface 121a of the first insertion groove 120a of the side fixing unit 12 to one surface of the second insertion groove 120b may be partitioned by the detector support 23 into a second section (length: L2) from the one surface 121a of the first insertion groove 120a to the first side portion 21 of the guide unit 20 and a third section (length: L3) from the second side portion 22 to the one surface 121b of the second insertion groove 120b.

A detecting device 3a whose horizontally extending length is L2 may be inserted into the second section in the receiving unit 11. A detecting device whose horizontally extending length is L3 may be inserted into the third section in the receiving unit 11. When the detecting device 3a whose horizontally extending length is L2 is inserted into the second section in the receiving unit 11, the guide unit 20 remains in a state before the detecting device 3a is inserted, a part of a one-side surface of the detecting device 3a is inserted into and fixed to the first insertion groove 120a, the other-side surface is supported by a one-side surface of the detector support 23, and thus the detecting device 3a may be fixed not to move. A part of the bottom of the detecting device 3a may be inserted into and fixed to the mounting unit 130 provided in the bottom fixing unit 13.

The mounting unit 130 may include a charging terminal 13a capable of charging the detecting device 3a. When the detecting device 3a is mounted in the mounting unit 130, the charging terminal 13a provided in the mounting unit 130 and a charging terminal 9 provided in the detecting device 3a are connected to charge the detecting device 3a.

The detecting device whose horizontally extending length is L3 may be inserted into the third section in the receiving unit 11. In this case, the guide unit 20 remains in a state that is the same before and after the detecting device is inserted, a one-side surface of the detecting device is supported by the detector support, and the other-side surface of the detecting device may be inserted into and fixed to the second insertion groove 120b. A part of the bottom of the detecting device can be inserted into and fixed to the mounting unit 130 provided in the bottom fixing unit 13.

In this manner, even when the detecting devices have various sizes, the detecting devices may be stably accommodated in the receiving unit 11 according to the structure of the guide unit 20. Therefore, it is possible to prevent the detecting device from being moved when the main body 4 is moved.

Figure 11:
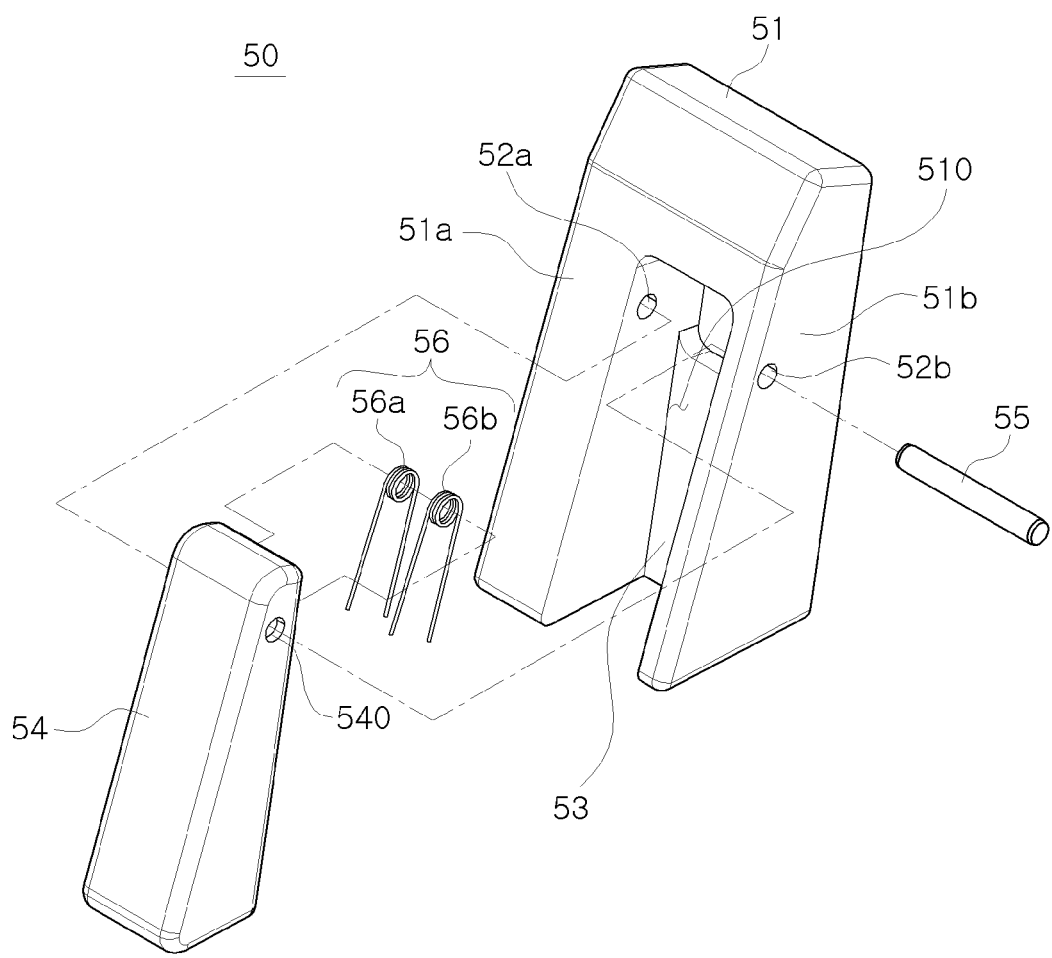
FIG. 11 is an exploded perspective view of a guide unit according to another embodiment.
Figure 12:
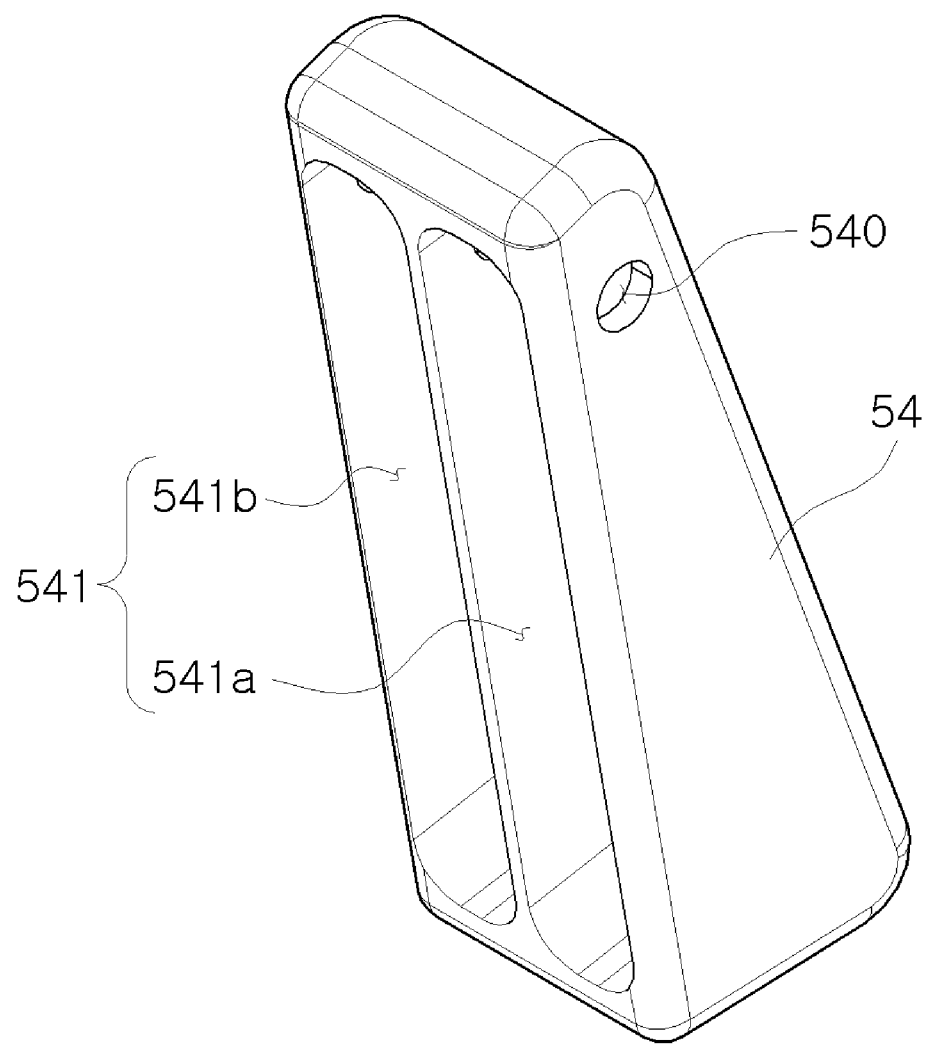
FIG. 12 is a diagram illustrating a detector guide according to another embodiment.

FIG. 11 is an exploded perspective view of a guide unit according to another embodiment. FIG. 12 is a diagram illustrating a detector guide according to another embodiment.

In a receiving device 10' according to another embodiment illustrated in FIGS. 11 to 16, configurations other than a detailed configuration of a guide unit 50 may be similar to those of FIGS. 1 to 10. Hereinafter, a detailed configuration of the guide unit 50 according to another embodiment will be described focusing on differences from the guide unit 20 illustrated in FIGS. 1 to 10.

As illustrated in FIGS. 11 and 12, the guide unit 50 according to another embodiment may include a body unit 51 and a detector support 54. The detector support 54 may be mounted in the body unit 51 and rotatable about a rotating shaft 55. The rotating shaft 55 may pass through a side of the body unit 51 and the detector support 54, and thus enable the detector support 54 to be tilted and mounted in the body unit 51.

The body unit 51 may include a receiving unit 510 in which the detector support 54 can be accommodated. The receiving unit 510 may be provided to correspond to a shape of the detector support 54. With respect to the receiving unit 510, the body unit 51 positioned in one side of the detector support 54 may be referred to as a first sidewall 51a, and the body unit 51 positioned in the other side may be referred to as a second sidewall 51b. A part of the body unit 51 facing one surface of the detector support 54 may be referred to as a support surface 53.

An elastic member 56 may be positioned between the detector support 54 and the support surface 53. The elastic member 56 may provide an elastic force such that the other side of the detector support 54 is away from the support surface 53.

As an example, the elastic member 56 may be provided in the form of a spring whose two arms protrude from a circular spring portion. Any one arm may support one surface of the detector support 54, and the other arm may support one surface of the detector support 54. The rotating shaft 55 may be inserted into the circular spring portion connecting two arms. A plurality of elastic members 56 may be provided. As an example, two elastic members 56 may be provided.

An elastic member receiving unit 541 in which the elastic member 56 can be accommodated may be provided on the other surface of the detector support 54. When the two elastic members 56 are provided, the elastic member receiving unit 541 may include a first elastic member receiving unit 541a in which any one elastic member is accommodated and a second elastic member receiving unit 541b in which the other elastic member is accommodated.

A rotating shaft insertion hole 540 into which the rotating shaft 55 can be inserted may be provided at a side of the detector support 54. Rotating shaft insertion holes 52a and 52b into which the rotating shaft 55 can be inserted may be formed in the first side portion 51a and the second side portion 51b of the body unit 51. The rotating shaft 55 may sequentially pass the rotating shaft insertion hole 52b formed in the second side portion 51b of the body unit 51, the rotating shaft insertion hole 540 formed in the detector support 54, and the rotating shaft insertion hole 52a formed in the first sidewall 51a. Therefore, the detector support 54 may be rotatably mounted in the body unit 51.

When the elastic member 56 is mounted in the rotating shaft 55, the rotating shaft 55 may sequentially pass the rotating shaft insertion hole 52b formed in the second side portion 51b of the body unit 51, the rotating shaft insertion hole 540 formed in the detector support 54, a spring portion of the elastic member 56, and the rotating shaft insertion hole 52a formed in the first sidewall 51a.

As illustrated in FIG. 2 to FIG. 4, the guide unit 50 may be mounted in a front inner side surface of the receiving device 10 forming the receiving unit 11. The guide unit 50 may be mounted in a rear inner side surface of the receiving device.

Figure 13:
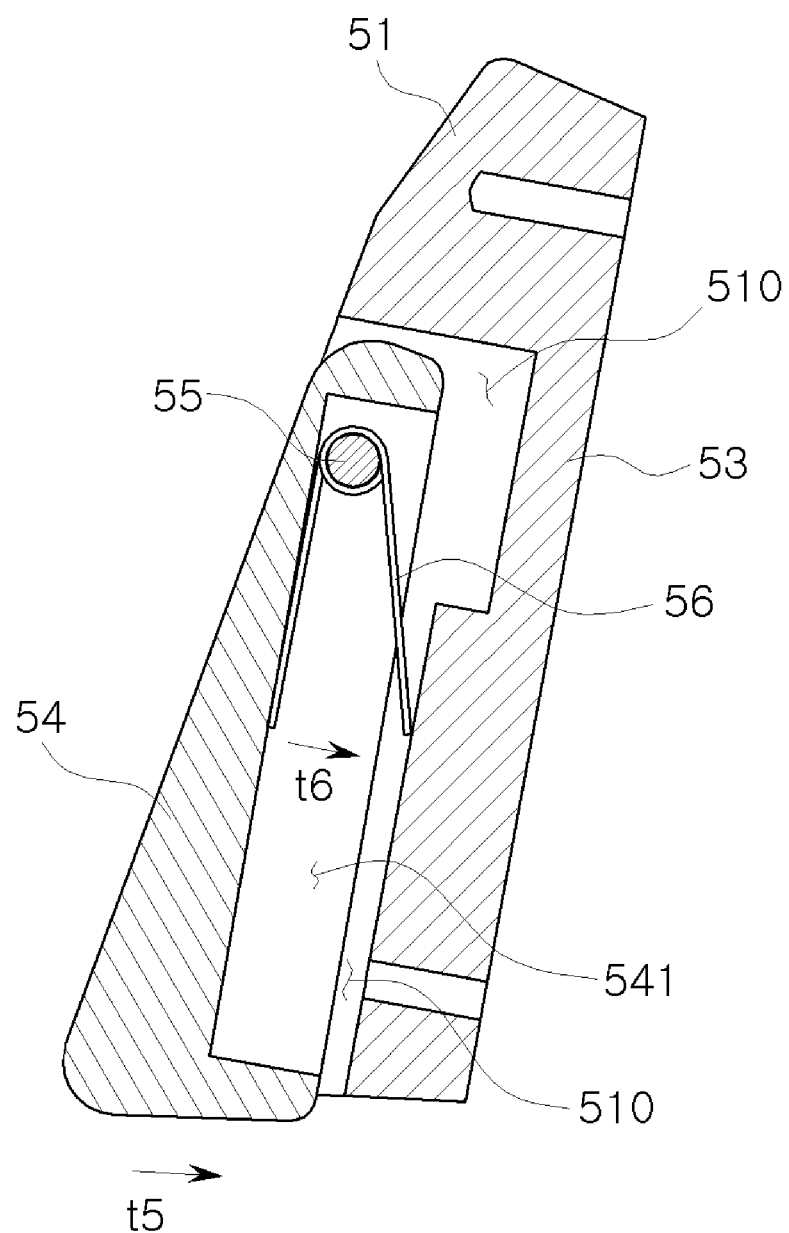
FIG. 13 is a side view of a guide unit when a detector guide according to another embodiment is in a first position.
Figure 14:
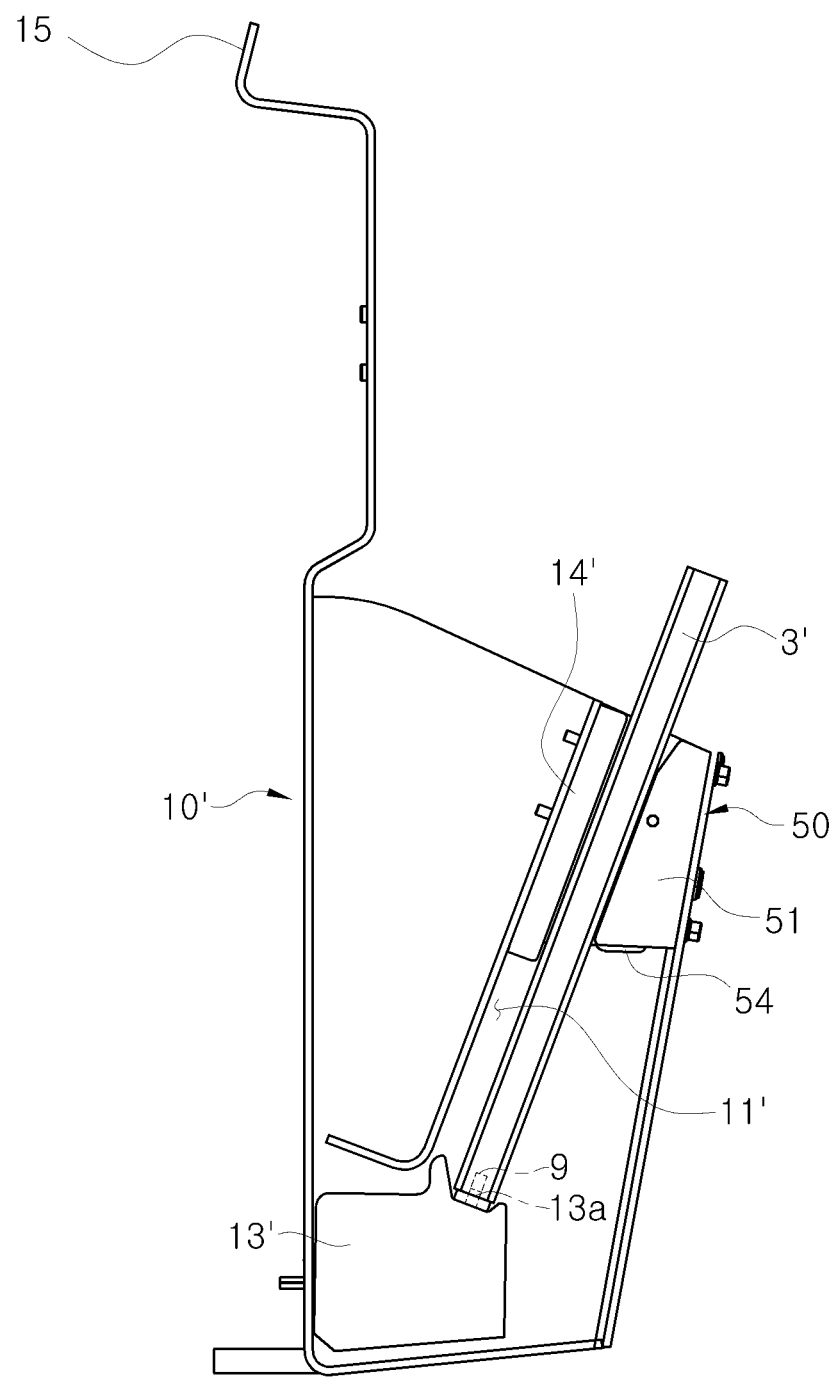
FIG. 14 is a side view of a receiving device when a detector guide according to another embodiment is in a first position.

FIG. 13 is a side view of a guide unit when a detector guide according to another embodiment is in a first position. FIG. 14 is a side view of a receiving device when a detector guide according to another embodiment is in a first position.

As illustrated in FIGS. 13 and 14, when a detecting device 3' is inserted into the receiving device 10' in which the guide unit 50 according to another embodiment is mounted, the other side of the detector support 54 may be tilted to move forward (direction t5: refer to FIG. 13) by the detecting device 3'.

The detector support 54 may be tilted in the direction t5 and accommodated in the receiving unit 510 positioned between the 12a first sidewall 51a and the second side portion 51b. In this case, a horizontally extending length of the detecting device 3' may correspond to a length from one surface of a first insertion groove of the side fixing unit 12 provided in the receiving device 10' to one surface of a second insertion groove.

In this case, an arm supporting the detector support 54 between two arms of the elastic member 56 positioned between the detector support 54 and the support surface 53 may move in a direction t6, and a distance between the two arms may decrease.

In the detecting device 3', a part of a side surface of the detecting device 3' may be slidably inserted into the first insertion groove and the second insertion groove formed in the first side guide and the second side guide. The detector support 54 may slide along the first insertion groove and the second insertion groove, and may slidably push the detector support 54 when coming in contact with the detector support 54. In the detector support 54, the other side of the detector support 54 may be tilted in the direction t5 with respect to the rotating shaft 55 due to a pushing force of the detecting device 3' and accommodated in the receiving unit 510 provided in the body unit 51.

In this manner, a part of a one-side surface of the detecting device 3' is inserted into the first insertion groove of the side fixing unit, a part of the other-side surface is inserted into the second insertion groove of the side fixing unit, and thus both sides may be fixed. Also, a bottom of the detecting device 3' may be mounted in and supported by the mounting unit 130 provided in the bottom fixing unit 13 that is positioned below a receiving unit 11'. Therefore, the detecting device 3' may be stably accommodated in the receiving unit 11' not to move even when the main body 4 is moved.

The mounting unit 130 includes a charging terminal 13a. When the detecting device 3' is mounted in the mounting unit 130, a charging terminal 9 provided in the detecting device 3' and the charging terminal 13a provided in the mounting unit 130 are connected to charge the detecting device 3'.

When the detector support 54 is inserted into the receiving unit 510 due to an external force, the detecting device 3' of a great horizontally extending length may also be easily inserted into the receiving unit 11' without intervention of the detector support 54.

Hereinafter, a case in which a detecting device of a short horizontally extending length is inserted into the receiving unit 11' will be described.

Figure 15:
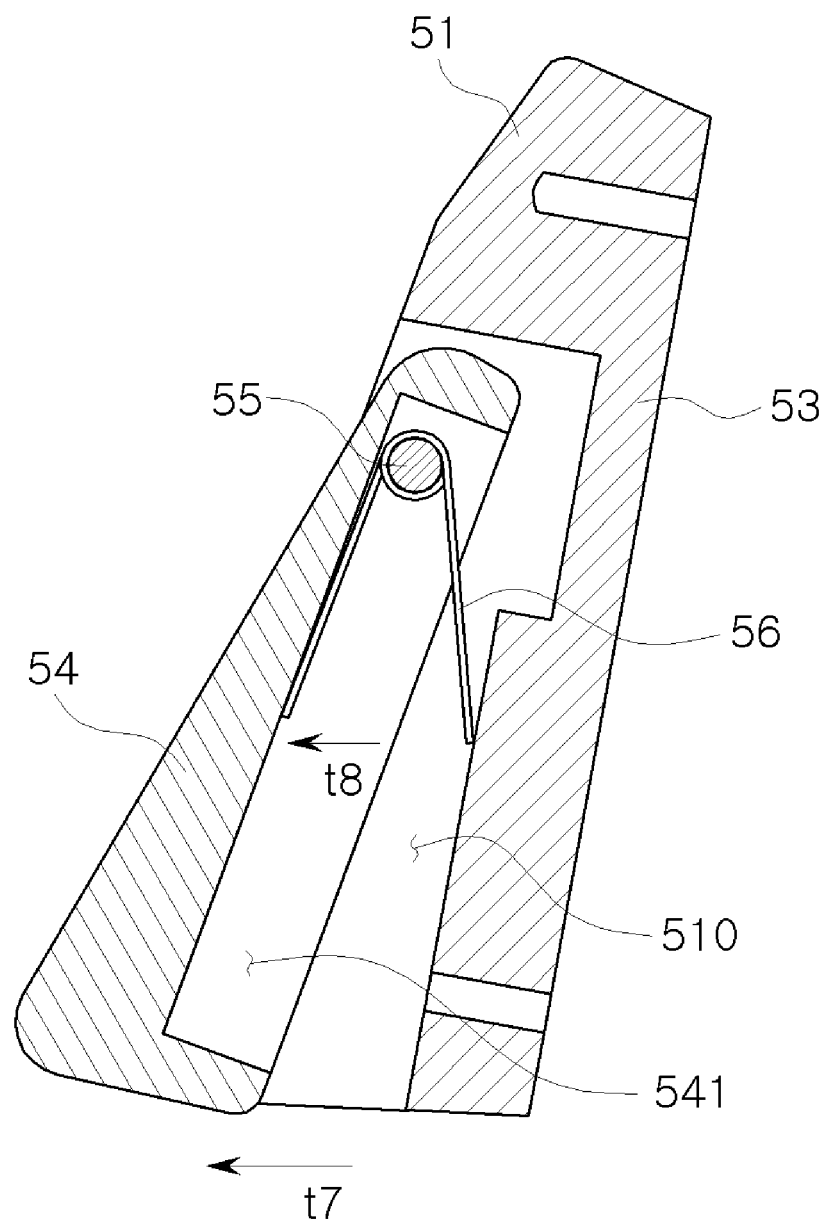
FIG. 15 is a side view of a guide unit when a detector guide according to another embodiment is in a second position.
Figure 16:
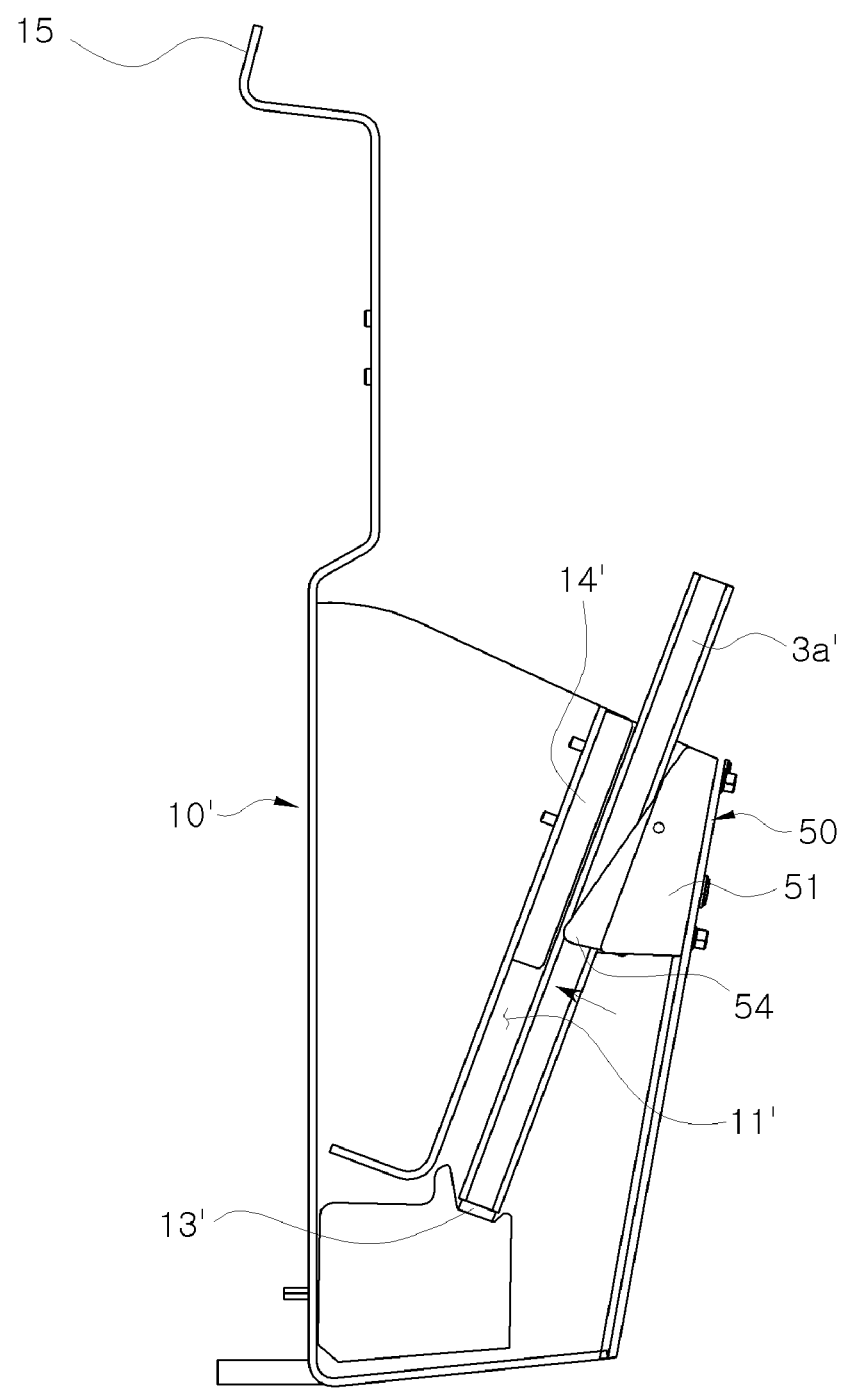
FIG. 16 is a side view of a receiving device when a detector guide according to another embodiment is in a second position.

FIG. 15 is a side view of a guide unit when a detector guide according to another embodiment is in a second position. FIG. 16 is a side view of a receiving device when a detector guide according to another embodiment is in a second position.

As illustrated in FIGS. 15 and 16, a detecting device 3a' according to another embodiment has a horizontally extending length that is any of a length from one surface of the first insertion groove of the side fixing unit to the first sidewall 51a of the guide unit 50 and a length from one surface of the second insertion groove to the second side portion 51b of the guide unit 50. Hereinafter, the horizontally extending length of the detecting device 3a' will be described as the length from one surface of the first insertion groove of the side fixing unit to the first sidewall 51a of the guide unit 50.

When the detecting device 3a' illustrated in FIGS. 13 and 15 is removed from the receiving unit 11', the detector support 54 may rotate in a direction t7 with respect to the rotating shaft 55 due to an elastic force of the elastic member 56, and be removed from the receiving unit 510 of the body unit 51. When the detector support 54 is tilted in the direction t7, at least a part of the elastic force of the elastic member 56 positioned between the detector support 54 and the support surface 53 is used to tilt the detector support 54. When the detector support 54 is tilted at a predetermined angle, the elastic member 56 may expand and have an elastic force smaller than that before the detector support 54 is tilted. When the detector support 54 is tilted in the direction t7, an arm of the elastic member 56 supporting an inner side surface of the detector support 54 may move in a direction t8 while the inner side surface of the detector support 54 is supported. The direction t7 and the direction t8 may be the same direction. Therefore, a distance between the arm supporting the inner side surface of the detector support 54 and the arm supporting the support surface 53 of the body unit 51 may increase.

As an example, when the detecting device 3a' whose horizontally extending length is L1 is removed from the receiving unit 11', a first section (length: L1) from one surface of the first insertion groove of the side fixing unit to one surface of the second insertion groove may be partitioned by the detector support 54 into a second section (length: L2) from the one surface of the first insertion groove to the first sidewall 51a of the guide unit 50 and a third section (length: L3) from the second side portion 51b to the one surface of the second insertion groove.

The detecting device 3a' whose horizontally extending length is L2 may be inserted into the second section in the receiving unit 11' and the detecting device whose horizontally extending length is L3 may be inserted into the third section in the receiving unit 11'. When the detecting device 3a' whose horizontally extending length is L2 is inserted into the second section in the receiving unit 11', the guide unit 50 remains in a state before the detecting device 3a' is inserted, a part of a one-side surface of the detecting device 3a' is inserted into and fixed to the first insertion groove, the other-side surface is supported by a one-side surface of the detector support 54, and thus the detecting device 3a' may be fixed not to move. A part of a bottom of the detecting device 3a' may be inserted into and fixed to a mounting unit provided in a bottom fixing unit 13'.

A detecting device whose horizontally extending length is L3 may be inserted into the third section in the receiving unit 11'. In this case, the guide unit 50 remains in a state that is the same before and after the detecting device is inserted, a one-side surface of the detecting device is supported by the detector support, and the other-side surface of the detecting device may be inserted into and fixed to the second insertion groove. A part of the bottom of the detecting device may be inserted into and fixed to the mounting unit provided in the bottom fixing unit 13'.

In this manner, when the detecting devices have various sizes, the detecting devices can be stably accommodated by the receiving unit 11' according to the structure of the guide unit 50. Therefore, it is possible to prevent the detecting device from being moved when the main body 4 is moved.

Figure 17:
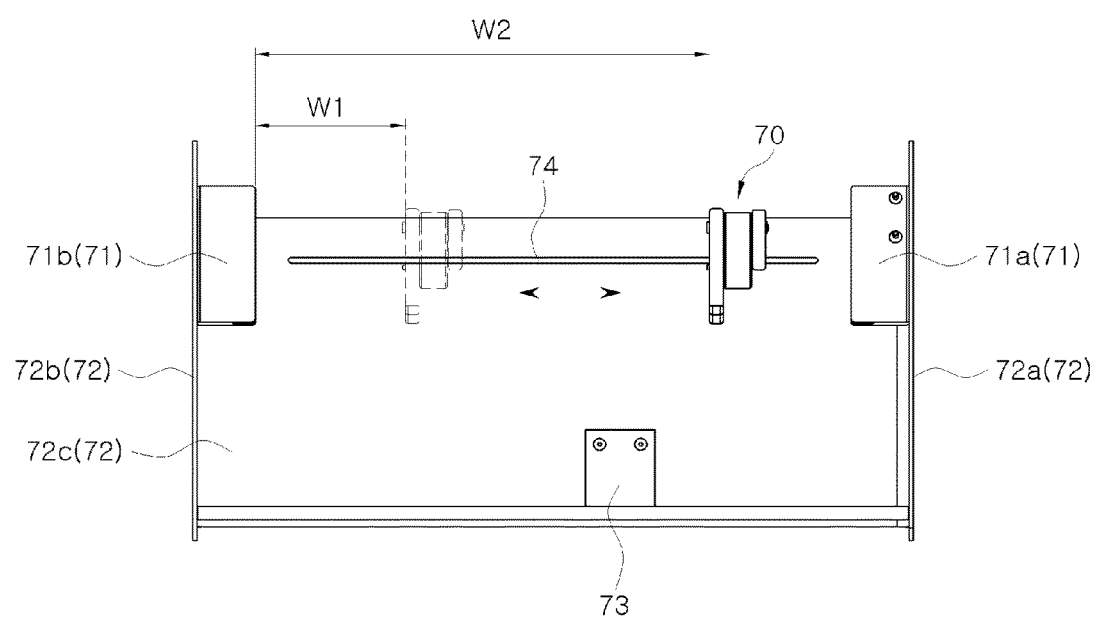
FIG. 17 is a diagram illustrating a part of a receiving device according to still another embodiment.

FIG. 17 is a diagram illustrating a part of a receiving device according to still another embodiment.

As illustrated in FIG. 17, a guide unit 70 provided in the receiving device according to still another embodiment is movable along a rail unit 74. The rail unit 74 may be provided on an inner side surface 72c of the receiving device forming the receiving unit. The rail unit 74 may extend in a horizontal direction. Side portions 72a and 72b are provided at both ends of the inner side surface 72c, respectively. Side fixing units 71a and 71b having an insertion hole into which a part of a side surface of the detecting device is slidably inserted may be provided in the side portions 72a and 72b. A direction in which the insertion hole extends may be perpendicular to a direction in which the rail unit 74 extends. A bottom fixing unit 73 configured to support a bottom of the detecting device may be provided in the lower part of the receiving device.

Since the guide unit 70 is horizontally movable along the rail unit, in order to fix both sides such that the detecting device is stably accommodated in the receiving unit, a position of the guide unit 70 may be moved according to a size of the detecting device.

As an example, in the guide unit 70, the guide unit 70 may be moved along the rail unit 74 in order to insert a detecting device having a horizontally extending length of w2 that is greater than w1 between the second side fixing unit 71b and the guide unit 70 when a distance from the second side fixing unit 71b is w1. The guide unit 70 may move to a point at which a length from the second side fixing unit 71b is w2. Therefore, the detecting device may be inserted between the second side fixing unit 71b and the guide unit 70, and the detecting device may be fixed not to move by side surfaces of the second side fixing unit 71b and the guide unit 70.

Meanwhile, the guide unit 70, which is movable along the rail unit 74, has a position that may be fixed by various types of stopper structures. Since the stopper structure of the related art can be used, a detailed description thereof will be omitted FIG. 18 is a diagram illustrating a part of a receiving device according to still another embodiment.

Figure 18:
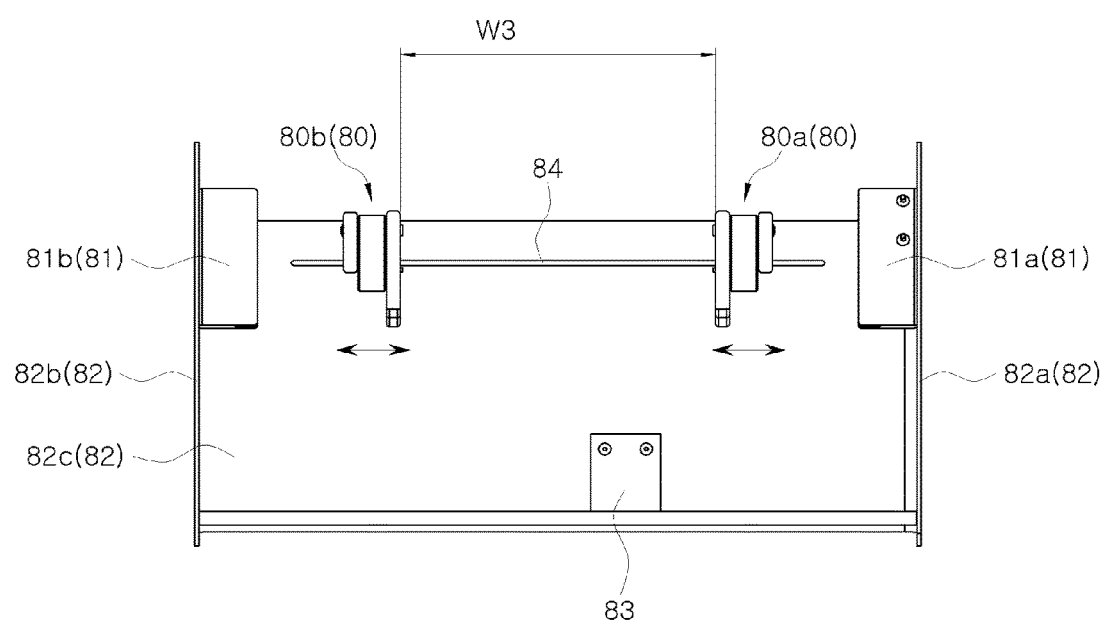
FIG. 18 is a diagram illustrating a part of a receiving device according to still another embodiment.

As illustrated in FIG. 18, the receiving device according to still another embodiment may include a plurality of guide units 80. The plurality of guide units 80 are movable along a rail unit 84 that extends in a horizontal direction. The rail unit 84 may be provided on an inner side surface 82c of the receiving device forming the receiving unit. Side portions 82a and 82b are provided at both ends of the inner side surface 82c, respectively. Side fixing units 81a and 81b having an insertion hole into which a part of a side surface of the detecting device is slidably inserted may be provided in the side portions 82a and 82b. A direction in which the insertion hole extends may be perpendicular to a direction in which the rail unit 84 extends. A bottom fixing unit 83 configured to support a bottom of the detecting device may be provided in the lower part of the receiving device.

According to the user's convenience, a guide unit adjacent to any of among the plurality of guide units may be separated at an interval to correspond to the horizontally extending length of the detecting device and then the detecting device may be inserted into the guide units.

For example, the guide unit 80 may include a first guide unit 80a and a second guide unit 80b. In order to accommodate a detecting device whose horizontally extending length is w3 in the receiving device, the user moves the first guide unit 80a or the second guide unit 80b along the rail unit 84, and when an interval between the first guide unit 80a and the second guide unit 80b is w3, fixes positions of the first guide unit 80a and the second guide unit 80b and may insert the detecting device therebetween. The detecting device may be fixed not to move even when the main body 4 is moved by a side surface of the first guide unit 80a and a side surface of the second guide unit 80b.

When positions of the first guide unit 80a and the second guide unit 80b are appropriately regulated, the detecting device may be inserted into spaces between the first side fixing unit 81a and the first guide unit 80a, between the first guide unit 80a and the second guide unit 80b, and between the second guide unit 80b and the second side fixing unit 81b. Therefore, the plurality of detecting devices may be accommodated in one receiving device.

The number of guide units that are movable along the rail unit 84 is not limited to the above. Meanwhile, since the stopper structure of fixing positions of the first guide unit 80a and the second guide unit 80b in the related art can be used, a detailed 3D description thereof will be omitted.

According to the above structure, detecting devices of various sizes may be stably accommodated in the receiving device having one receiving unit.

While the receiving device provided in the mobile X-ray imaging apparatus has been described above, the structure in which the guide unit is provided in the receiving device is a structure in which a plate-shaped object of a different size may be stably accommodated in one receiving unit. Therefore, the structure may be utilized as a space for receiving a detector for X-ray imaging and utilized in other fields.

According to the embodiment, the detector may be stably supported even when a detector having a smaller size than the receiving unit is accommodated in the receiving unit by a detector fixing device provided in the receiving device. Since receiving units for accommodating detectors of different sizes are not separately provided, the receiving device has good space utilization.

What is claimed is:

1. A receiving device, for an X-ray imaging apparatus, in which X-ray detectors of different sizes are accommodable, comprising:
    an X-ray detector accommodation space configured to accommodate one of a first X-ray detector and a second X-ray detector having a size smaller than a size of the first X-ray detector, the first X-ray detector and the second X-ray detector provided to be inserted into and withdrawn from the X-ray detector accommodation space;
    a fixing unit having an insertion groove into which a side surface of the one of the first X-ray detector and the second X-ray detector is slidably inserted; and
    a guide unit provided on an inner surface of the X-ray detector accommodation space, the guide unit comprising:
        a rotating shaft; and
        an X-ray detector support connected to the rotating shaft so that the X-ray detector support is rotatable about the rotating shaft,
    wherein when the first X-ray detector is inserted into the X-ray detector accommodation space, the X-ray detector support is rotated about the rotating shaft, and
    when the second X-ray detector is inserted into the X-ray detector accommodation space, the X-ray detector support is not rotated about the rotating shaft and configured to guide a side surface of the second X-ray detector.

2. The receiving device according to claim 1, wherein the guide unit further includes an elastic member between the X-ray detector support and an inner side surface of the X-ray detector accommodation space, and the elastic member to provide an elastic force pushing the X-ray detector support away from the inner side surface of the X-ray detector accommodation space.

3. The receiving device according to claim 2, wherein, when the first X-ray detector is inserted into the X-ray detector accommodation space, the X-ray detector support is pressed by the first X-ray detector and rotated toward the inner side surface of the X-ray detector accommodation space.

4. The receiving device according to claim 2, wherein the guide unit further includes a support bracket between the X-ray detector support and the inner side surface of the X-ray detector accommodation space to support the elastic member.

5. The receiving device according to claim 1, wherein the guide unit further includes side portions having a shaft insertion hole, respectively, to receive the rotating shaft so that the X-ray detector support is rotatably mounted on the side portions by the rotating shaft, the side portions are mounted on the inner surface of the X-ray detector accommodation space.

6. The receiving device according to claim 5, wherein, when the second X-ray detector is inserted into the X-ray accommodation space, at least one side surface of the second X-ray detector is supported by one of the side portions.

7. The receiving device according to claim 5, wherein the guide unit further includes a restricting portion to restrict a movement of the X-ray detector support by restricting a movement angle of the X-ray detector support.

8. The receiving device according to claim 7, wherein the restricting portion is provided as part of a concentric circle having a same center of rotation as a circle drawn by ends of the X-ray detector support.

9. The receiving device according to claim 7, wherein the restricting portion includes a guide groove, and one of the side portions includes an intervention unit, which is inserted into the guide groove of the restricting portion so that the movement angle of the X-ray detector support is restricted by a movement of the intervention unit inside of the guide groove.

10. The receiving device according to claim 1, further comprising a bottom fixing unit in a bottom portion of the X-ray detector accommodation space, the bottom fixing unit configured to support one of a bottom surface of the first X-ray detector and a bottom surface of the second X-ray detector when the one of the first X-ray detector and the second X-ray detector is inserted into the X-ray detector accommodation space.

11. The receiving device according to claim 10, wherein the first X-ray detector includes a charging terminal and the second X-ray detector includes a charging terminal, and the bottom fixing unit includes a charging terminal corresponding to the charging terminal of the first X-ray detector and the charging terminal of the second X-ray detector, and when one of the first X-ray detector and the second X-ray detector is inserted into the X-ray detector accommodating space, the one of the first X-ray detector and the second X-ray detector is electrically charged through the charging terminal of the one of the first X-ray detector and the second X-ray detector and the corresponding charging terminal of the bottom fixing unit.

12. The receiving device according to claim 1, wherein the fixing unit includes a pair of side fixing units, the pair of the slide fixing units respectively having the insertion groove into which both side surfaces of the first X-ray detector are slidably inserted.

13. The receiving device according to claim 12, wherein the pair of side fixing units is respectively mounted to a left side and a right side of the X-ray detector accommodation space.

14. The receiving device according to claim 1, further comprising a rail unit mounted on an inner side surface of the X-ray detector accommodation space, and the X-ray detector support is movable along the rail unit.

15. The receiving device according to claim 1, wherein the X-ray detector support includes a plurality of X ray detector supports and the rotating shaft includes a plurality of rotating shafts, which the plurality of X-ray detector supports are rotatably connected to and the plurality of X-ray detector supports are configured to be rotatable with respect to the plurality of rotating shafts, respectively, to support the first X-ray detector and the second X-ray detector.

16. An X-ray imaging apparatus, comprising:
a movable main body;
an X-ray generating unit mounted to the movable main body and configured to generate X-rays; and
an X-ray detector receiving unit mounted to the movable main body, the X-ray detector receiving unit comprising:
an X-ray detector accommodation space configured to accommodate one of a first X-ray detector and a second X-ray detector having a size smaller than a size of the first X-ray detector, the first X-ray detector and the second X-ray detector provided to be inserted into and withdrawn from the X-ray detector accommodation space;
a fixing unit having an insertion groove into which a side surface of the one of the first X-ray detector and the second X-ray detector is slidably inserted; and
a guide unit provided on an inner surface of the X-ray detector accommodation space, the guide unit comprising:
a rotating shaft; and
an X-ray detector support connected to the rotating shaft so that the X-ray detector support is rotatable about the rotating shaft,
wherein
when the first X-ray detector is inserted into the X-ray detector accommodation space, the X-ray detector support is rotated about the rotating shaft, and
when the second X-ray detector is inserted into the X-ray detector accommodation space, the X-ray detector support is not rotated about the rotating shaft and configured to guide a side surface of the second X-ray detector.

17. The X-ray imaging apparatus according to claim 16, wherein the guide unit further includes an elastic member between the X-ray detector support and an inner side surface of the X-ray detector accommodation space.

18. The X-ray imaging apparatus according to claim 17, wherein the elastic member has a directional elastic force that increases a distance between the X-ray detector support and the inner side surface of the X-ray detector accommodation space.

19. The X-ray imaging apparatus according to claim 16, wherein, when the first X-ray detector having a horizontal length corresponding to a horizontal length of the X-ray detector accommodation space is inserted into the X-ray detector accommodation space, the X-ray detector support is pressed by the first X-ray detector, and a distance between the X-ray detector support and an inner side surface of the X-ray detector accommodation space decreases.

20. The X-ray imaging apparatus according to claim 16, wherein the X-ray detector support is rotatably mounted to the inner surface of the X-ray detector accommodation space.

21. The X-ray imaging apparatus according to claim 16, wherein the fixing unit further includes a side fixing unit mounted to a left side of the X-ray detector accommodation space and a side fixing unit mounted to a right side of the X-ray detector accommodation space, and a part of at least one side surface of the first X-ray detector is respectively inserted into the side fixing unit of the left side and the side fixing unit of the right side and fixed thereto.

22. The X-ray imaging apparatus according to claim 16, wherein the fixing unit further includes a bottom fixing unit in a bottom portion of the X-ray detector accommodation space, the bottom fixing unit comprising a mounting groove in which the one of the first X-ray detector and the second X-ray detector is mounted.

* * * * *